United States Patent
Kamikawa et al.

(10) Patent No.: US 11,419,696 B2
(45) Date of Patent: Aug. 23, 2022

(54) CONTROL DEVICE, CONTROL METHOD, AND MEDICAL SYSTEM

(71) Applicant: SONY CORPORATION, Tokyo (JP)

(72) Inventors: Yasuhisa Kamikawa, Tokyo (JP); Jun Arai, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 577 days.

(21) Appl. No.: 16/333,120

(22) PCT Filed: Aug. 14, 2017

(86) PCT No.: PCT/JP2017/029252
§ 371 (c)(1),
(2) Date: Mar. 13, 2019

(87) PCT Pub. No.: WO2018/055950
PCT Pub. Date: Mar. 29, 2018

(65) Prior Publication Data
US 2019/0328481 A1    Oct. 31, 2019

(30) Foreign Application Priority Data

Sep. 23, 2016  (JP) .............................. JP2016-185146

(51) Int. Cl.
*A61B 90/00*    (2016.01)
*A61B 90/20*    (2016.01)
(Continued)

(52) U.S. Cl.
CPC .............. *A61B 90/37* (2016.02); *A61B 1/002* (2013.01); *A61B 90/20* (2016.02); *A61B 90/361* (2016.02);
(Continued)

(58) Field of Classification Search
CPC ....... A61B 90/37; A61B 90/20; A61B 90/361; A61B 90/25; A61B 90/50; A61B 1/002;
(Continued)

(56) References Cited

U.S. PATENT DOCUMENTS 5,961,456 A * 10/1999 Gildenberg .......... H04N 13/275
600/429
6,675,040 B1    1/2004 Cosman
(Continued)

FOREIGN PATENT DOCUMENTS

JP    2004-157614 A    6/2004
JP    2005-135344 A    5/2005
(Continued)

OTHER PUBLICATIONS

International Search Report dated Oct. 27, 2017 in PCT/JP2017/029252 citing documents AA, AB and AP therein, 3 pages.

*Primary Examiner* — Sean D Mattson
(74) *Attorney, Agent, or Firm* — Xsensus LLP

(57) ABSTRACT

There is provided a control device that decides at least one medical image as a medical image to display or save from among medical images taken by a plurality of imaging devices, on a basis of imaging device status information that includes information about a position or an attitude for at least one of the plurality of imaging devices.

19 Claims, 14 Drawing Sheets

(51) Int. Cl.
*A61B 1/002* (2006.01)
*G16H 30/20* (2018.01)

(52) U.S. Cl.
CPC ........ *G16H 30/20* (2018.01); *A61B 2090/367* (2016.02); *A61B 2090/371* (2016.02); *A61B 2090/373* (2016.02); *A61B 2090/376* (2016.02); *A61B 2090/3782* (2016.02)

(58) Field of Classification Search
CPC ........ A61B 2090/367; A61B 2090/371; A61B 2090/373; A61B 2090/376; A61B 2090/3782; A61B 2090/309; A61B 2090/3784; A61B 2090/502; A61B 2090/0818; A61B 2034/2048; A61B 2034/2059; A61B 2034/2051; A61B 2034/2055; A61B 2017/00216; G16H 30/20
See application file for complete search history.

(56) References Cited

U.S. PATENT DOCUMENTS

| | | | | |
|---|---|---|---|---|
| 8,221,304 B2 * | 7/2012 | Shioda | ............... | A61B 1/042 600/102 |
| 2003/0179308 A1 * | 9/2003 | Zamorano | ............... | A61B 5/00 348/333.12 |
| 2004/0138556 A1 * | 7/2004 | Cosman | ............... | A61B 90/10 600/424 |
| 2007/0197896 A1 * | 8/2007 | Moll | ............... | A61B 1/00039 600/407 |
| 2007/0236514 A1 * | 10/2007 | Agusanto | ............... | G16H 50/50 345/646 |
| 2008/0183071 A1 * | 7/2008 | Strommer | ............... | G06T 7/80 600/424 |
| 2014/0276684 A1 * | 9/2014 | Huennekens | .. | A61B 17/320758 606/7 |
| 2015/0098551 A1 * | 4/2015 | Kwak | ............... | A61B 6/4494 378/91 |
| 2015/0173846 A1 | 6/2015 | Schneider et al. | | |
| 2015/0190204 A1 * | 7/2015 | Popovi | ............... | A61B 1/00149 600/424 |
| 2015/0332465 A1 * | 11/2015 | Schmidt | ............... | A61B 34/20 348/169 |
| 2016/0360117 A1 * | 12/2016 | Elefteriu | ............... | A61B 90/20 |
| 2021/0030479 A1 * | 2/2021 | Marti | ............... | A61B 34/20 |

FOREIGN PATENT DOCUMENTS

| | | | |
|---|---|---|---|
| JP | 5347089 B1 | | 11/2013 |
| JP | 2015119323 A | * | 6/2015 |
| WO | WO 2014/037953 A2 | | 3/2014 |

* cited by examiner

[Fig. 1]
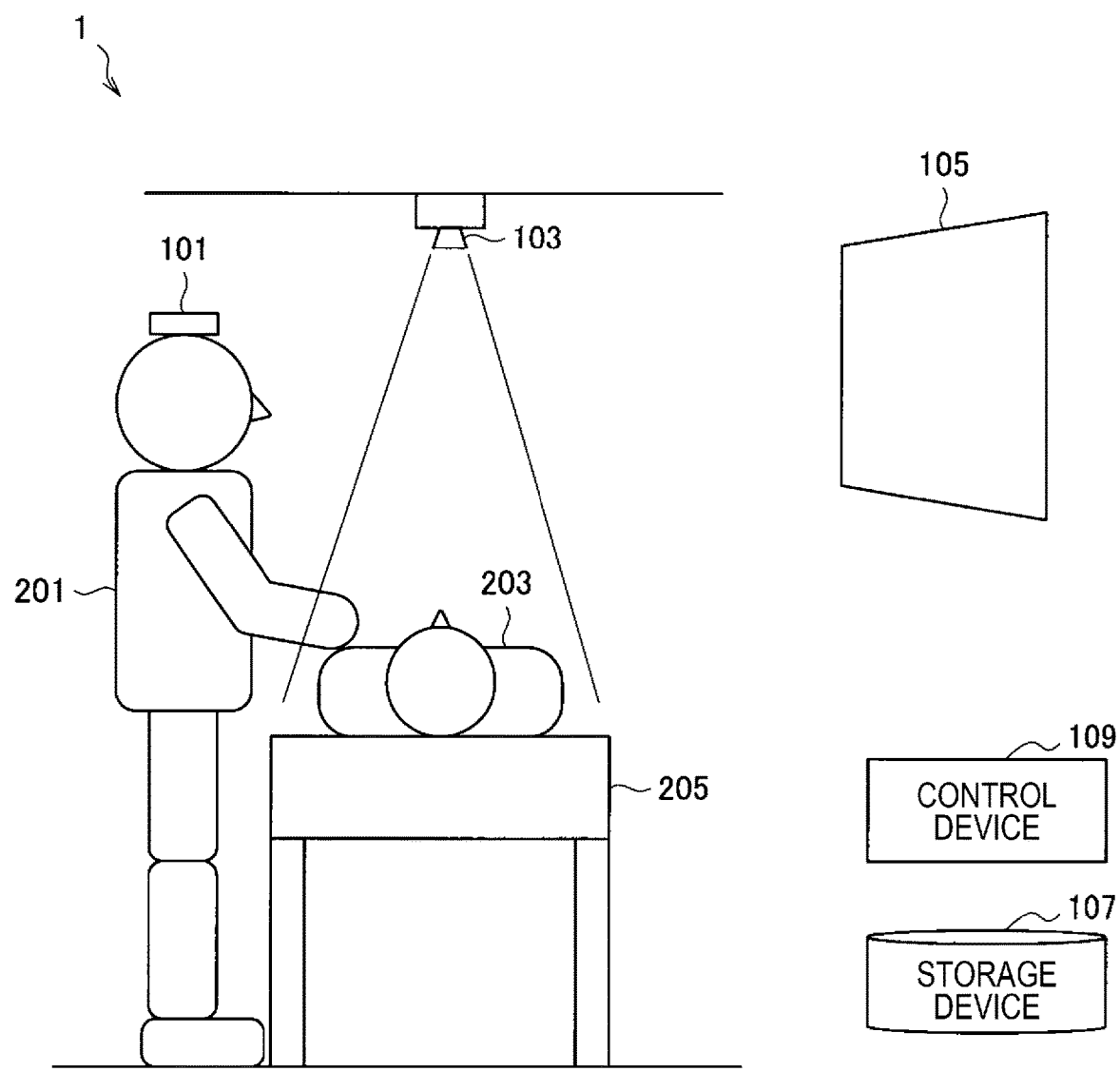

[Fig. 2]
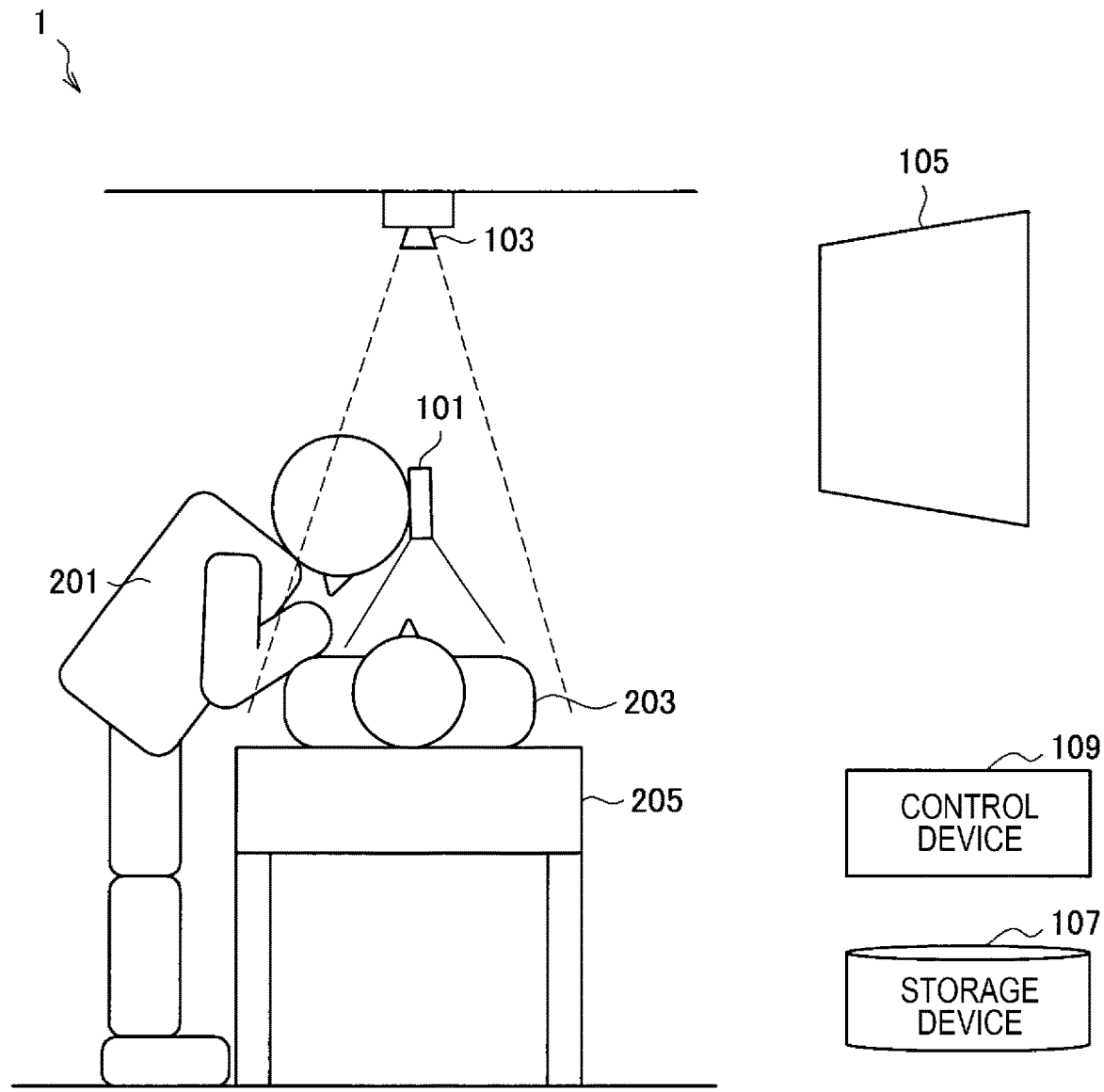

[Fig. 3]
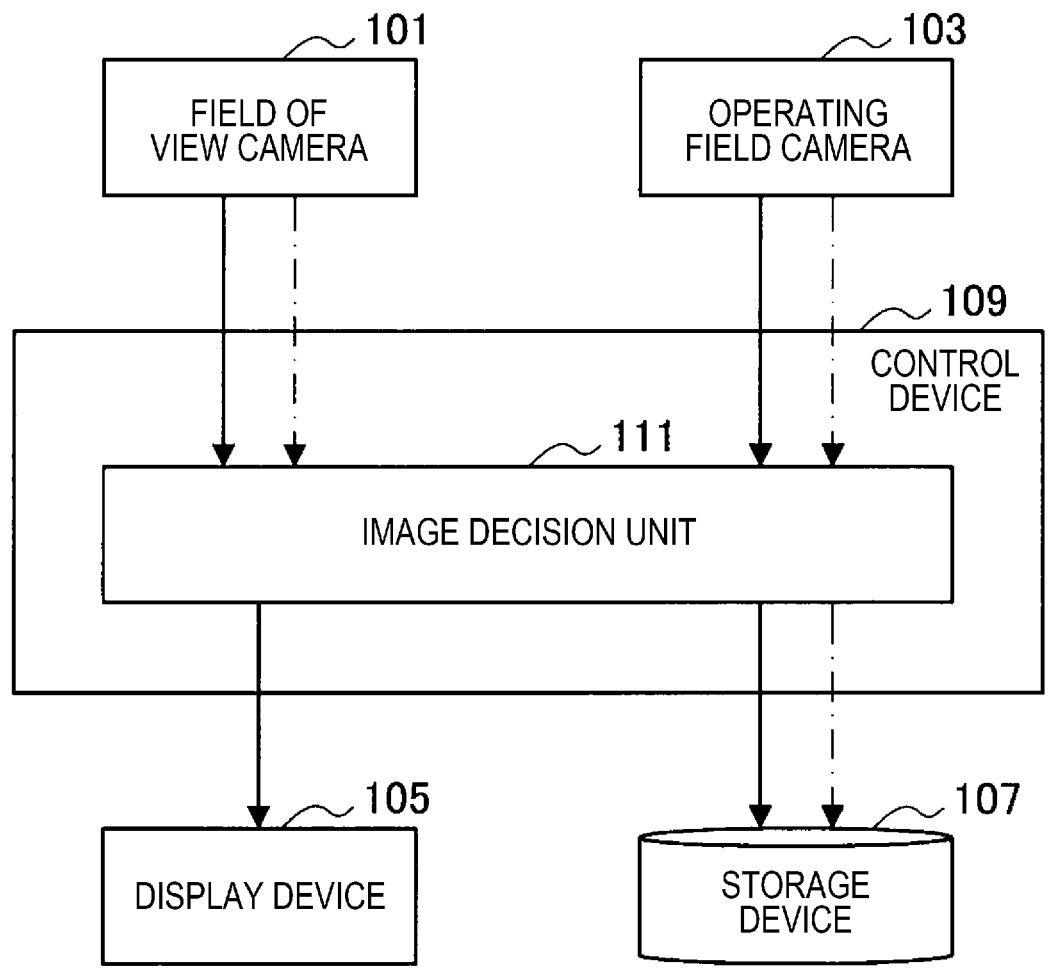

[Fig. 4]
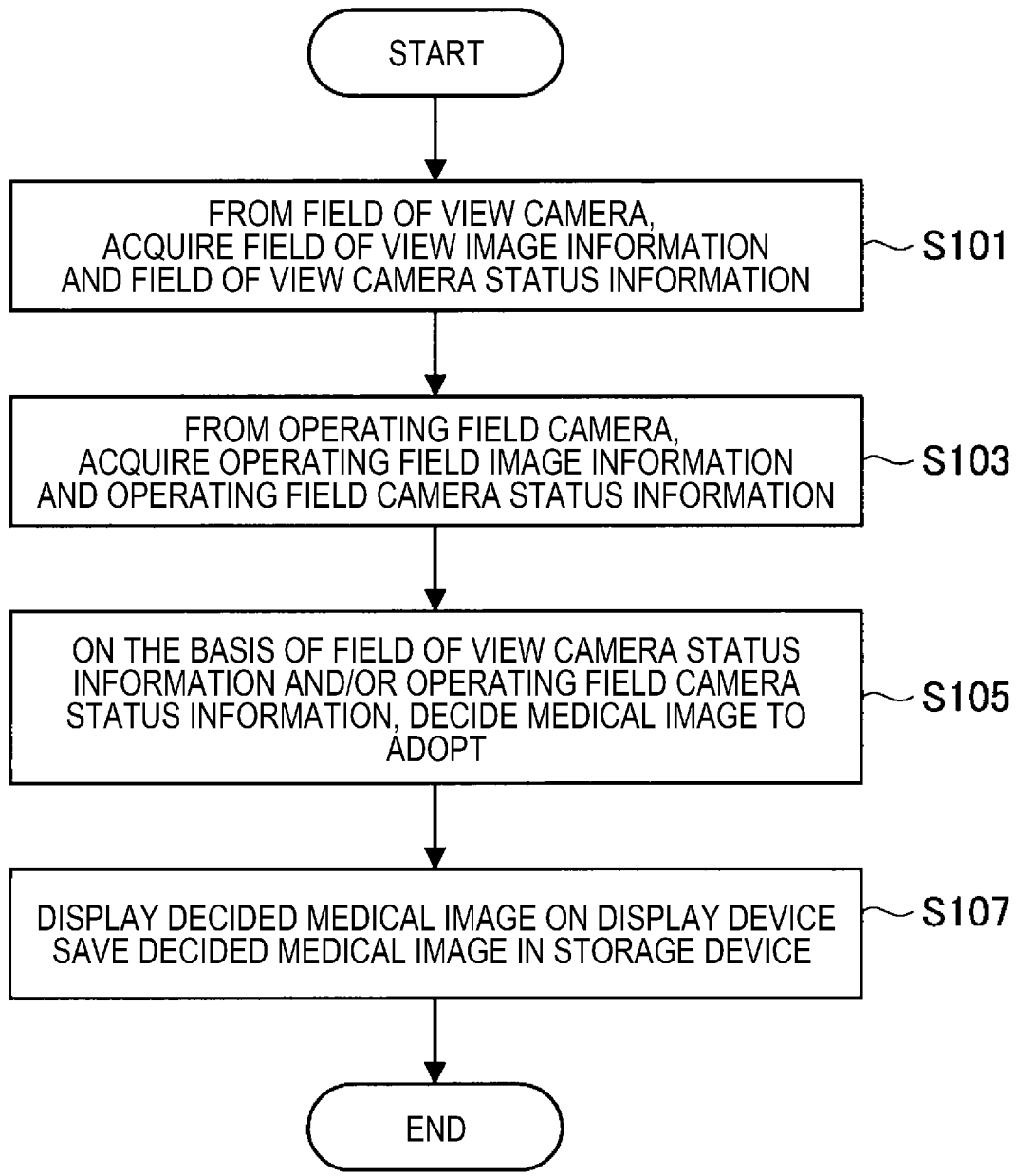

[Fig. 5]
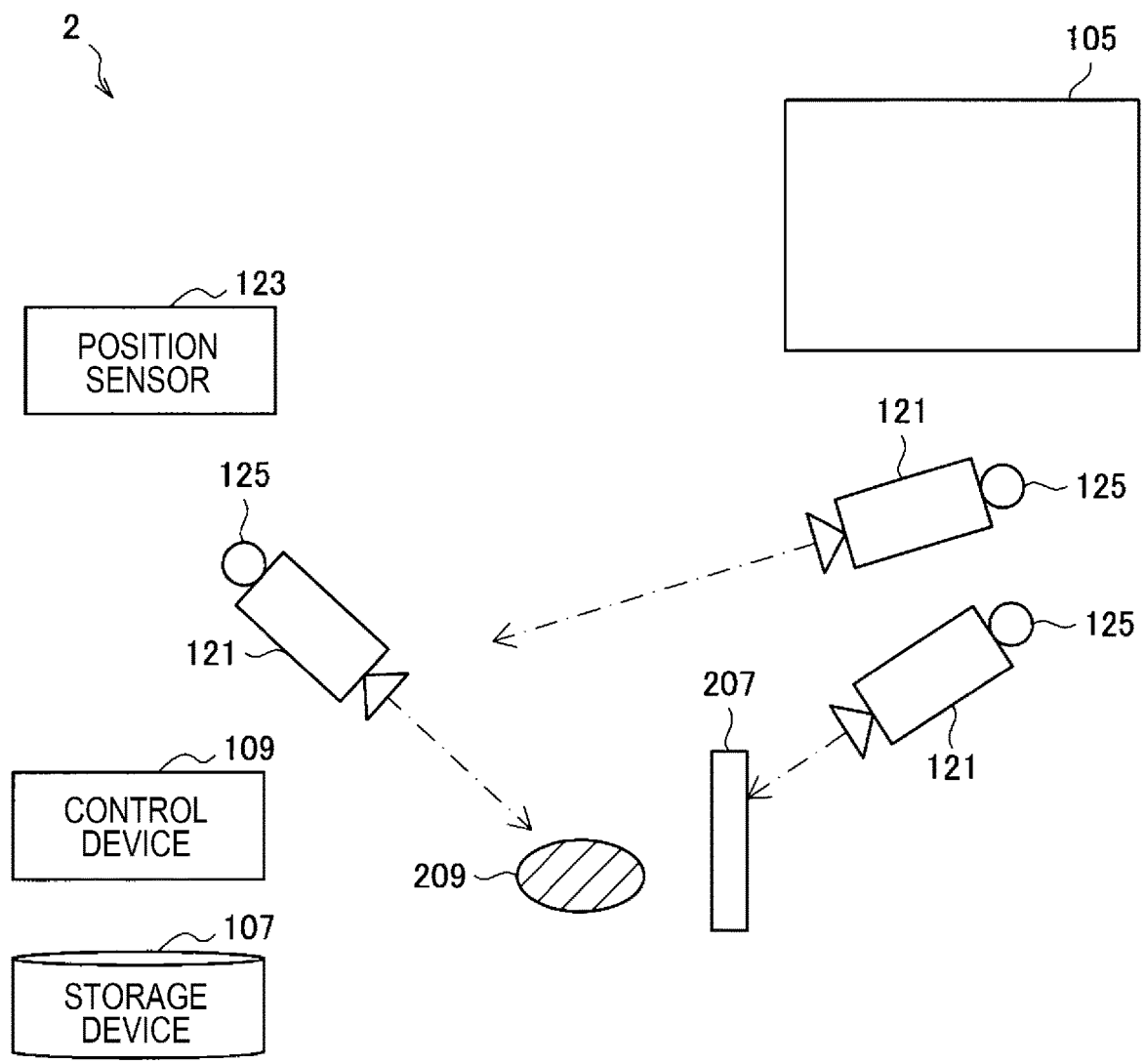

[Fig. 6]
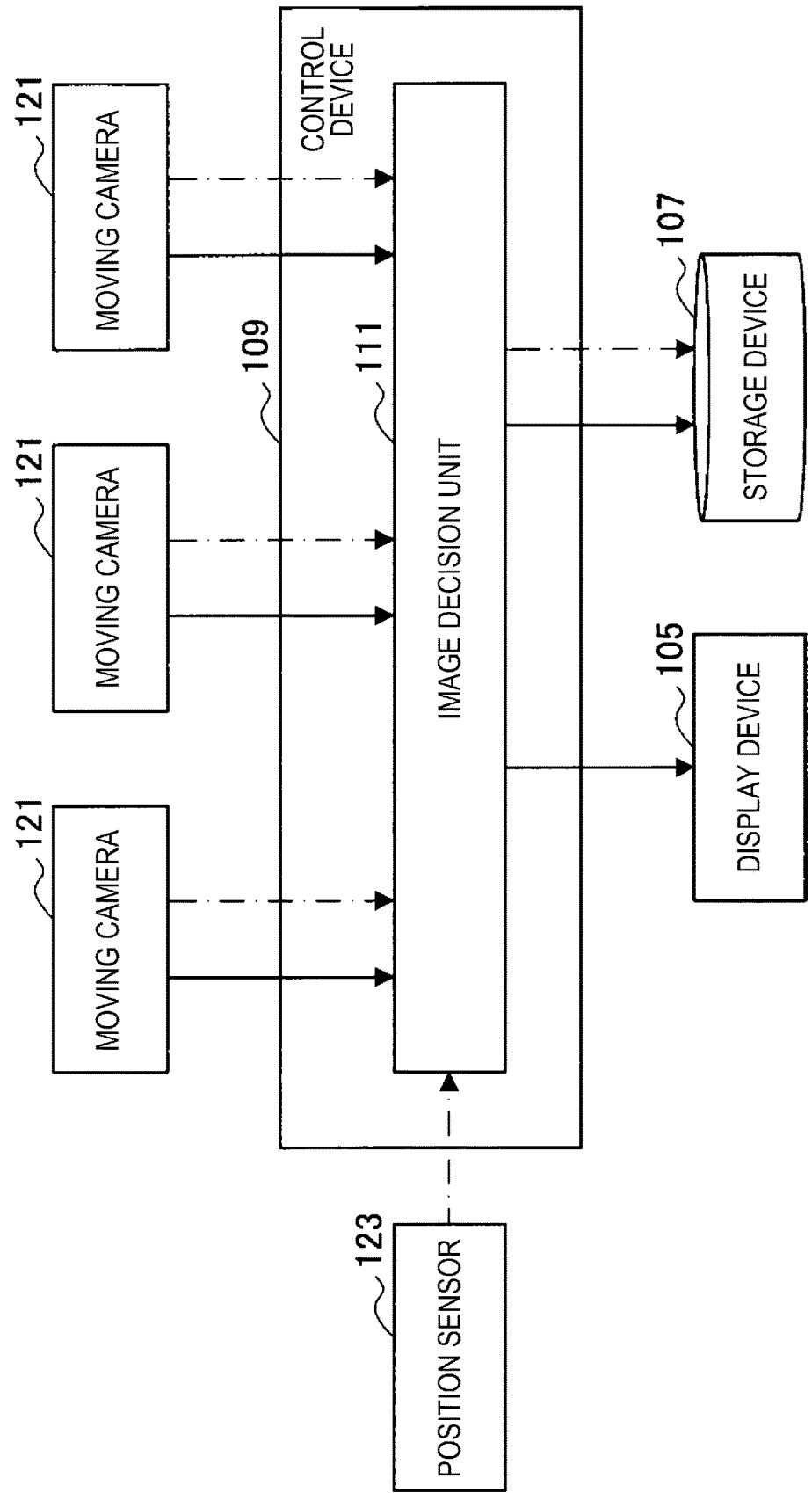

[Fig. 7]
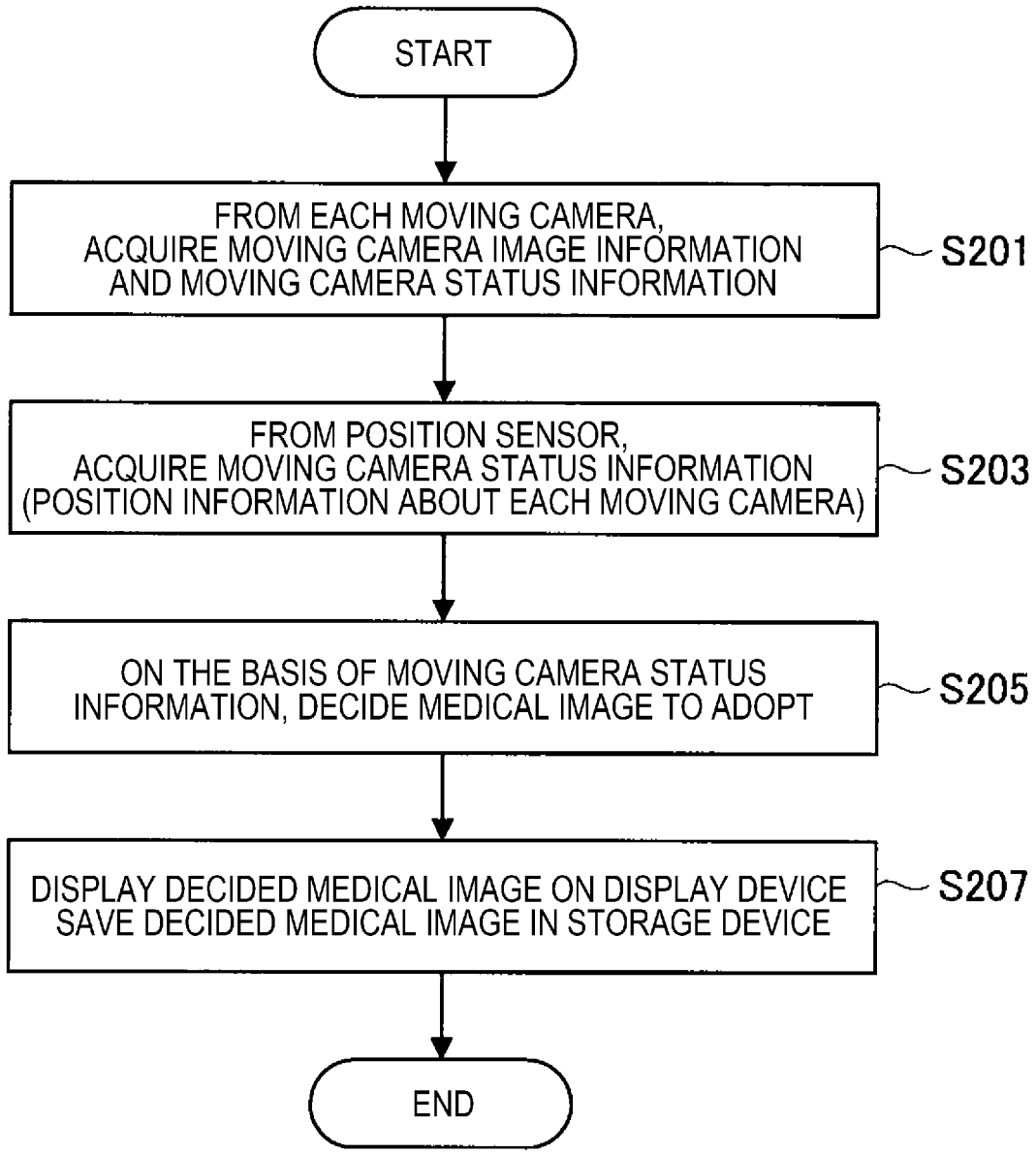

[Fig. 8]
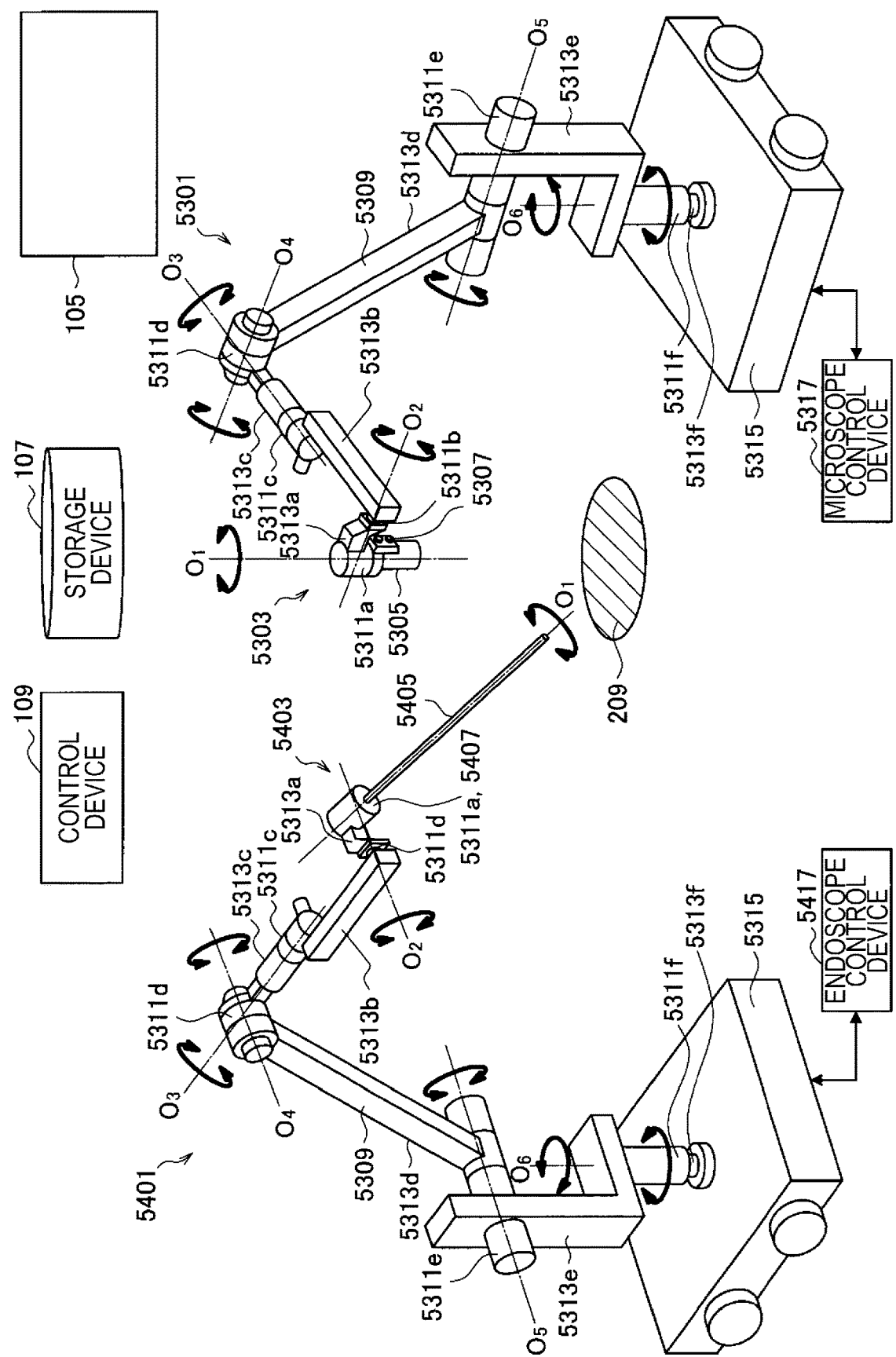

[Fig. 9]
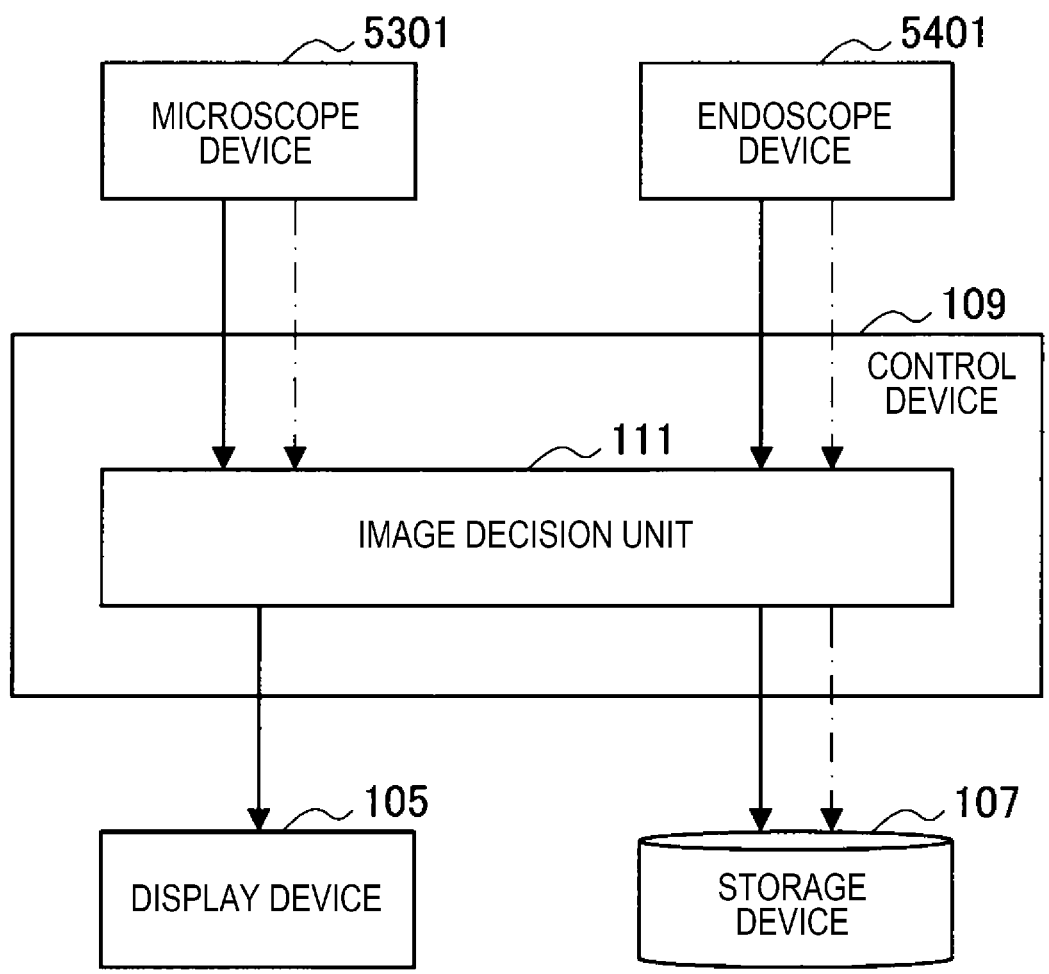

[Fig. 10]
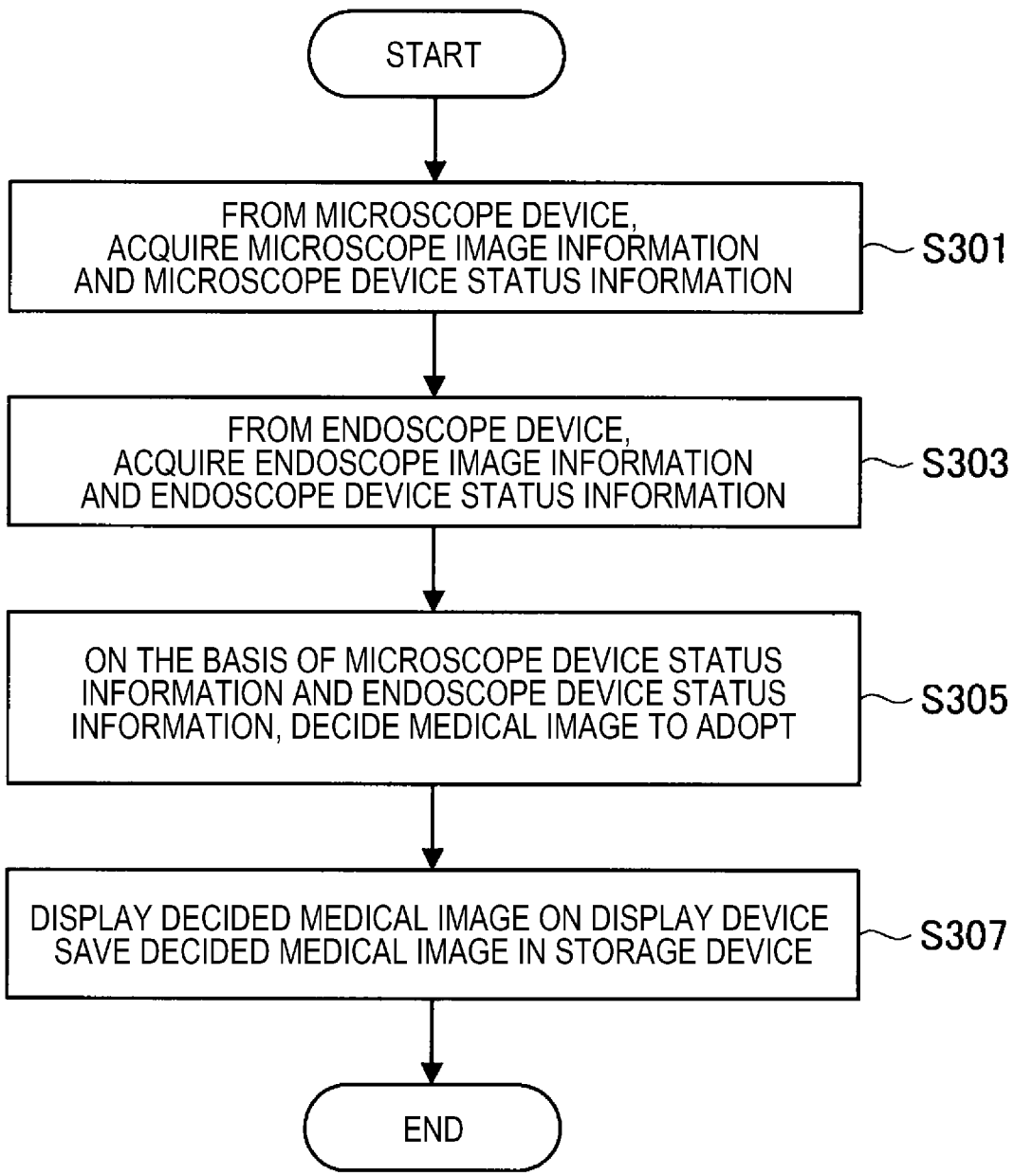

[Fig. 11]
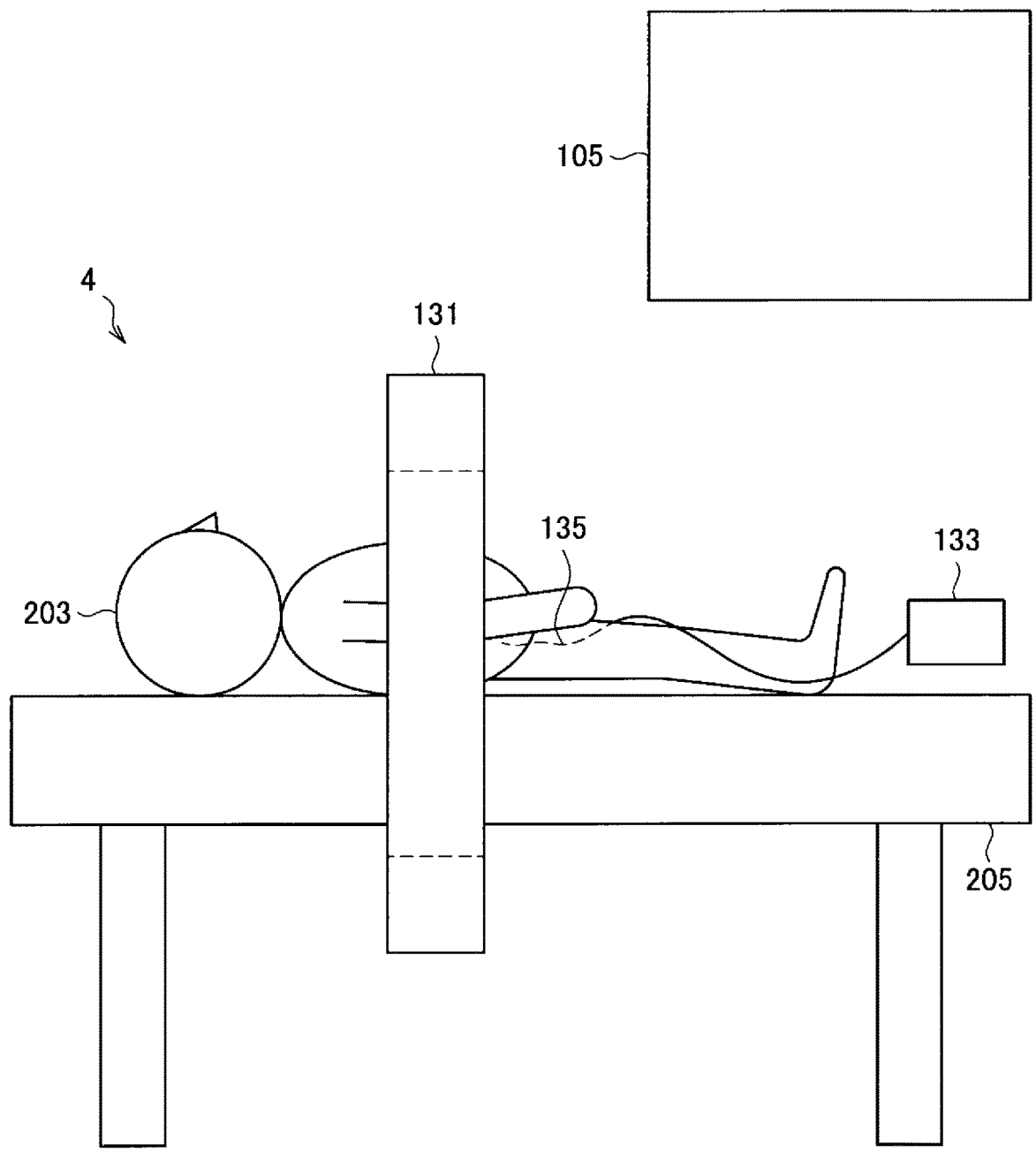

[Fig. 12]
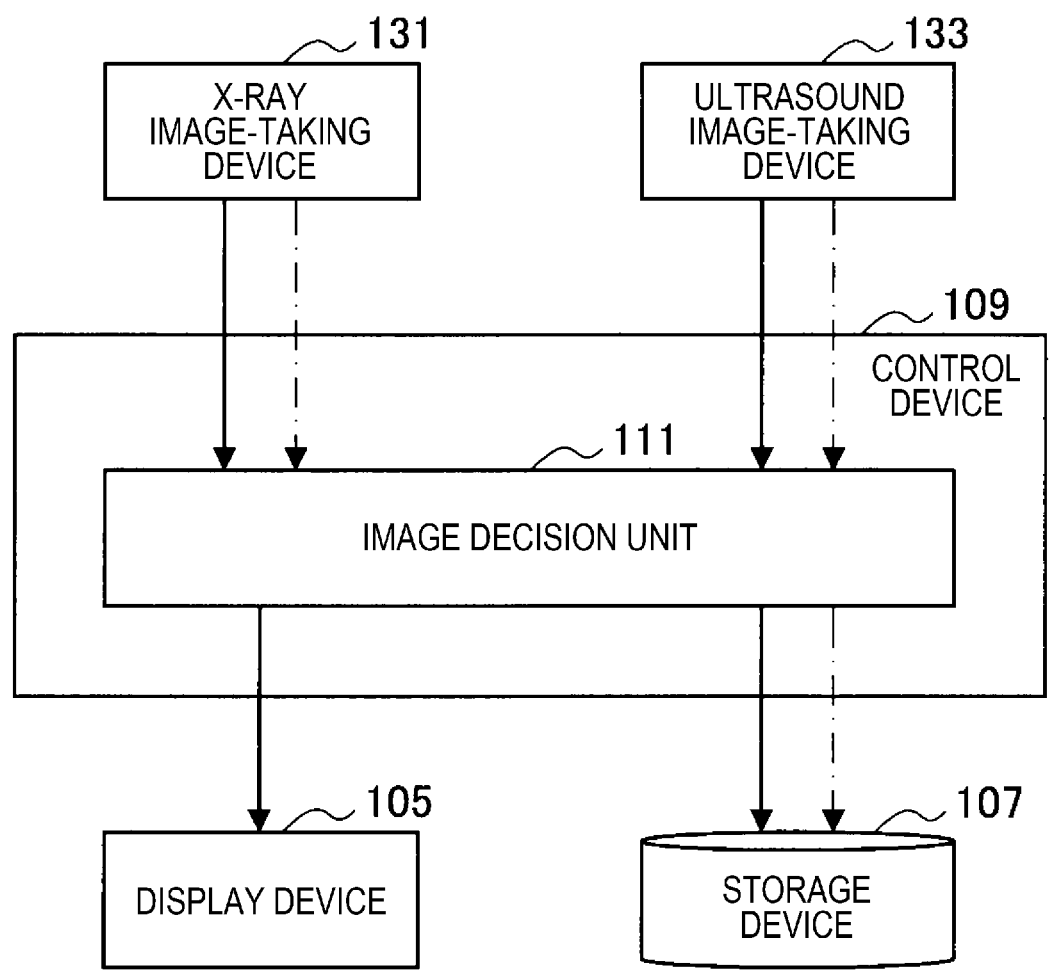

[Fig. 13]
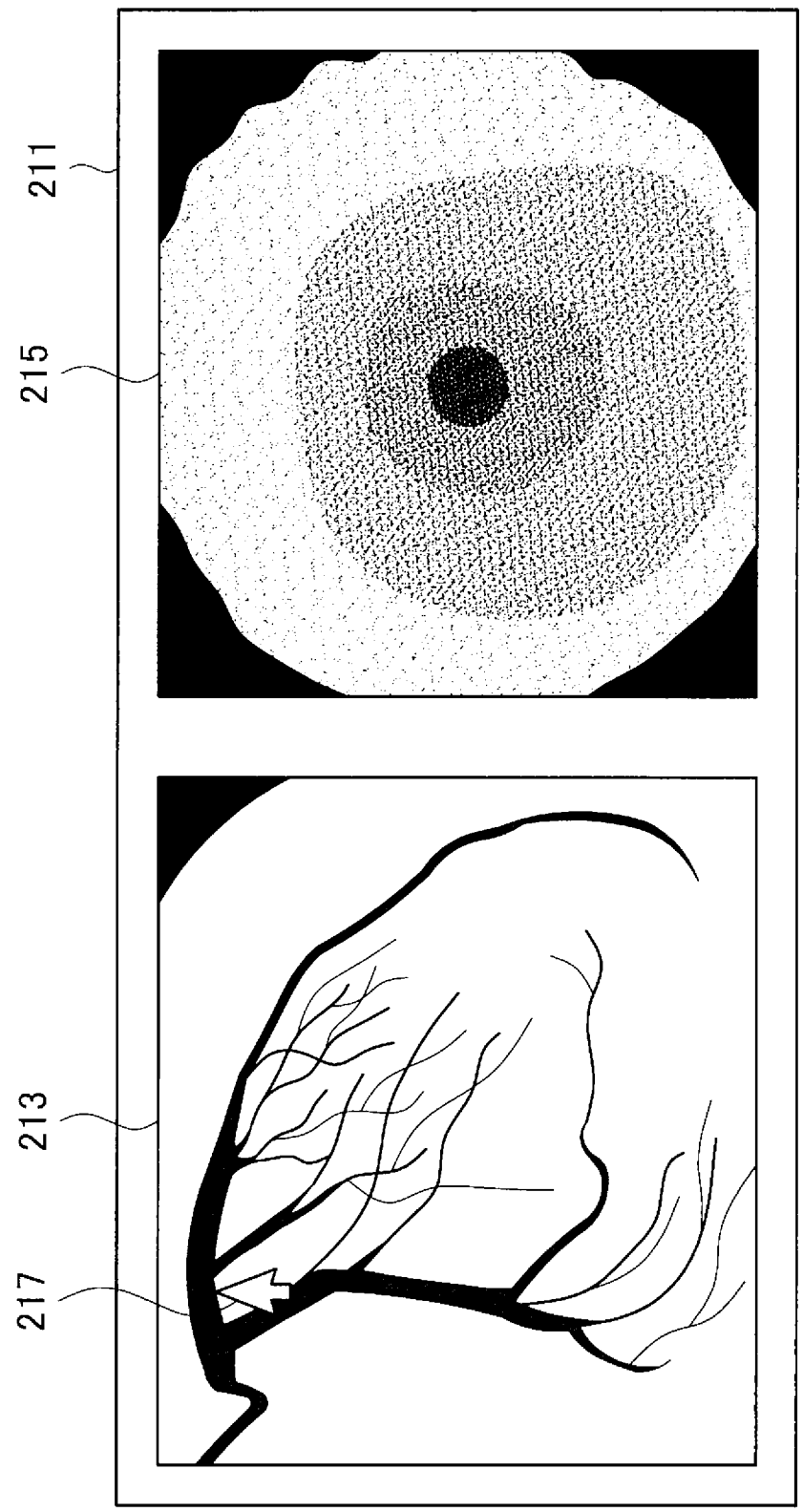

[Fig. 14]
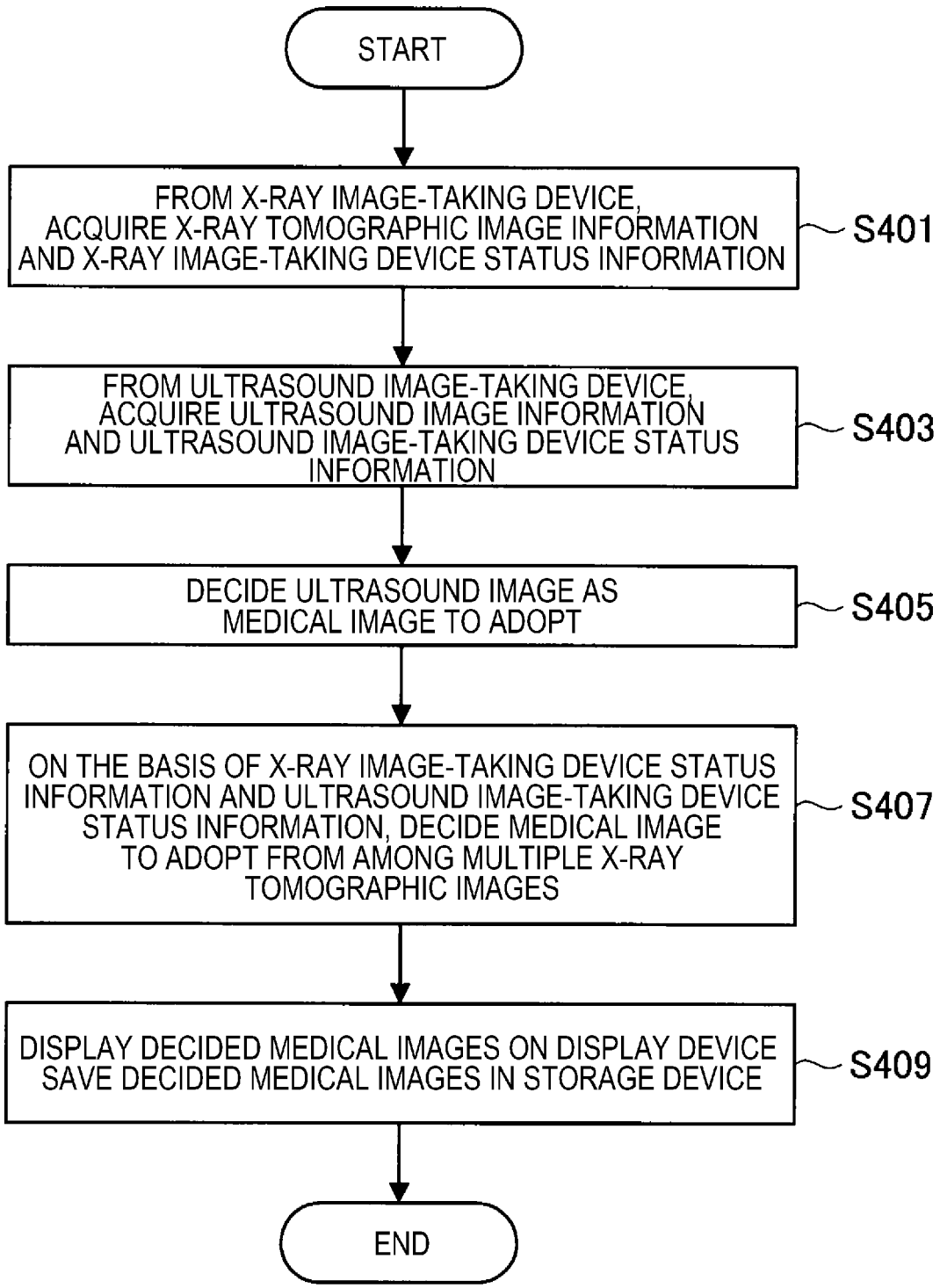

CONTROL DEVICE, CONTROL METHOD, AND MEDICAL SYSTEM

CROSS REFERENCE TO RELATED APPLICATIONS

This application claims the benefit of Japanese Priority Patent Application JP 2016-185146 filed Sep. 23, 2016, the entire contents of which are incorporated herein by reference.

TECHNICAL FIELD

The present disclosure relates to a control device, a control method, and a medical system.

BACKGROUND ART

Generally in medical procedures such as surgeries and examinations, images related to the medical procedure (medical images) are saved for the purpose of recording the treatment details and the medical case, or for the education of young doctors and the like. At this point, multiple different types of medical images, such as endoscopic images, X-ray images, and ultrasonic images, for example, are often taken in the middle of a medical procedure. However, if all of these medical images are saved, even medical images which are unwanted in the first place, such as images that do not clearly depict the lesion to be observed, for example, will be saved, and there is a possibility of creating complicated work such as editing after the surgery.

Accordingly, technology for more appropriately saving multiple medical images taken during a medical procedure is being developed. For example, Patent Literature 1 discloses a technology in which, when saving a composite image obtained by compositing multiple medical images taken during a medical procedure into a single image, a composition pattern for compositing the multiple medical images is decided on the basis of a result of analyzing the type of the imaging device used to take each medical image as well as each of the medical images themselves, and the composite image is generated and saved in accordance with the composition pattern. With such technology, Patent Literature 1 makes it possible to save appropriate composite images automatically, without manual work.

CITATION LIST

Patent Literature

PTL 1: JP 5347089B

SUMMARY

Technical Problem

However, as described above, with the technology described in Patent Literature 1, the composition pattern for the composite image is decided (that is, the medical images to save are decided) using the results of analyzing the medical images. Since image analysis typically requires intensive computational processing, with the technology described in Patent Literature 1, it is difficult to rapidly conduct the series of processes of deciding a composition pattern, and generating and saving a composite image in accordance with the composition pattern. In addition, if the medical images are not clear, there is a risk that appropriately deciding a composition pattern using the results of image analysis may become impossible. In this way, with the technology described in Patent Literature 1, there is a possibility that the process of deciding which medical images to save may not be conducted reliably.

Accordingly, the present disclosure proposes a new and improved control device, control method, and medical system enabling medical images to be managed more appropriately.

Solution to Problem

According to an embodiment of the present disclosure, there is provided a medical control device for a medical imaging system including processing circuitry that selects at least one medical image from among a plurality of medical images obtained by a plurality of medical imaging devices, the selection being based on medical imaging device status information that includes three dimensional information of at least one of the plurality of medical imaging devices, and outputs the selected at least one medical image from the plurality of medical images obtained by the plurality of medical imaging devices.

Further, according to an embodiment of the present disclosure, there is provided a control method, including: selecting at least one medical image from among a plurality of medical images obtained by a plurality of medical imaging devices, the selecting being based on medical imaging device status information that includes three dimensional information of at least one of the plurality of medical imaging devices and outputting the selected at least one medical image from the plurality of medical images obtained by the plurality of medical imaging devices.

Further, according to an embodiment of the present disclosure, there is provided a medical system, including: a plurality of medical imaging devices; and processing circuitry that selects at least one medical image from among a plurality of medical images obtained by the plurality of medical imaging devices, the selection being based on medical imaging device status information that includes information about a three-dimensional posture of at least one of the plurality of medical imaging devices, and outputs the selected at least one medical image from the plurality of medical images obtained by the plurality of medical imaging devices.

According to an embodiment of the present disclosure, at least one medical image to display or save is decided from among medical images taken by multiple imaging devices, on the basis of imaging device status information that includes information about the position and/or attitude (three dimensional position and/or three dimensional posture) for at least one of the multiple imaging devices. In other words, when deciding which medical images to display or save, results from image analysis are not used. Since the images to display or save may be decided without conducting image analysis, the trouble that may occur in the case of using image analysis results as described above may be avoided, making it possible to manage medical images more appropriately.

Advantageous Effects of Invention

According to an embodiment of the present disclosure as described above, it becomes possible to manage medical images more appropriately. Note that the effects described above are not necessarily limitative. With or in the place of the above effects, there may be achieved any one of the

BRIEF DESCRIPTION OF DRAWINGS

FIG. 1 is a diagram illustrating a diagrammatic configuration of a system according to a first embodiment.

FIG. 2 is a diagram illustrating a diagrammatic configuration of a system according to a first embodiment.

FIG. 3 is a block diagram illustrating a functional configuration of a system according to a first embodiment.

FIG. 4 is a flowchart illustrating an example of a processing sequence of a control method according to a first embodiment.

FIG. 5 is a diagram illustrating a diagrammatic configuration of a system according to a second embodiment.

FIG. 6 is a block diagram illustrating a functional configuration of a system according to a second embodiment.

FIG. 7 is a flowchart illustrating an example of a processing sequence of a control method according to a second embodiment.

FIG. 8 is a diagram illustrating a diagrammatic configuration of a system according to a third embodiment.

FIG. 9 is a block diagram illustrating a functional configuration of a system according to a third embodiment.

FIG. 10 is a flowchart illustrating an example of a processing sequence of a control method according to a third embodiment.

FIG. 11 is a diagram illustrating a diagrammatic configuration of a system according to a fourth embodiment.

FIG. 12 is a block diagram illustrating a functional configuration of a system according to a fourth embodiment.

FIG. 13 is a diagram illustrating an exemplary display on a display device in a system according to a fourth embodiment.

FIG. 14 is a flowchart illustrating an example of a processing sequence of a control method according to a fourth embodiment.

DESCRIPTION OF EMBODIMENTS

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

Hereinafter, the description will proceed in the following order.

1. First embodiment
1-1. Configuration of system
1-2. Control method
2. Second embodiment
2-1. Configuration of system
2-2. Control method
3. Third embodiment
3-1. Configuration of system
3-2. Control method
4. Fourth embodiment
4-1. Configuration of system
4-2. Control method
5. Conclusion and supplementary remarks

1. First Embodiment

1-1. Configuration of System

A configuration of a system according to a first embodiment of the present disclosure will be described with reference to FIGS. 1 to 3. FIGS. 1 and 2 are diagrams illustrating a diagrammatic configuration of a system according to the first embodiment. FIG. 3 is a block diagram illustrating a functional configuration of a system according to the first embodiment. FIGS. 1 and 2 illustrate a situation in which a system 1 according to the first embodiment is used to capture the state of surgery when a surgeon 201 performs surgery on a patient 203 lying on an operating table 205.

Referring to FIGS. 1 to 3, the system 1 according to the first embodiment is provided with a first camera 101 attached to the head of the surgeon 201, a second camera 103 which is installed on the ceiling of the operating room and which captures the state of surgery, a display device 105 which is installed inside the operating room and which displays a medical image taken by the first camera 101 or a medical image taken by the second camera 103, a storage device 107 that saves image information corresponding to a medical image displayed on the display device 105, and a control device 109 that decides which medical image to display on the display device 105 and which image information to save in the storage device 107. Note that the storage device 107 and the control device 109 may be installed inside the operating room or installed in another location separate from the operating room. However, from the perspective of not cluttering the inside of the operating room, the storage device 107 and the control device 109 preferably are installed in a location outside the operating room. Note that in this specification, saving image information is also simply referred to as saving an image for the sake of convenience.

During surgery, there may be demand to capture the state of how various treatments are being performed on the operating site of the patient 203 during surgery, for the purpose of recording the treatment details and the medical case, or for the education of young doctors and the like. The system 1 is a medical image management system that manages medical images taken by the first camera 101 or the second camera 103 for such purposes.

The first camera 101 is a compact camera worn on the head of the surgeon 201 with a headband, for example. Alternatively, the first camera 101 may be a camera mounted on a device worn on the head of the surgeon 201, such as a head-mounted display or a spectacle-style wearable device. By being worn on the head of the surgeon 201, the first camera 101 is able to take a medical image corresponding to the field of view of the surgeon 201. Hereinafter, the first camera 101 will also be designated the field of view camera (e.g. point of view camera, head mount camera, or the like) 101.

In the first embodiment, the field of view camera 101 is provided with an attitude sensor for detecting the attitude of the field of view camera 101. The attitude sensor is a gyro sensor, for example. However, the present embodiment is not limited to such an example, and any of various types of known sensors used to detect attitude may also be used as the attitude sensor.

The field of view camera 101 transmits information (field of view image information) about the medical image that the field of view camera 101 itself has taken (hereinafter also called an field of view image) to the control device 109 on a certain interval corresponding to the frame rate of the medical image, for example. Also, at this time, the field of view camera 101 associates field of view camera status information indicating the status of the field of view camera 101 with the field of view image information as metadata, and transmits the metadata together with the field of view image information to the control device 109. In the first embodiment, the field of view camera status information at least includes information about the attitude of the field of view camera 101 detected by the above attitude sensor. Note that in FIG. 3, as well as in FIGS. 6, 9, and 12 described later, the movement of information about medical images is indicated by solid arrows, whereas the movement of metadata associated with the information about medical images is indicated by chain-line arrows.

The second camera 103 is a camera that captures the state of surgery from a fixed point, otherwise known as an operating field camera. Hereinafter, the second camera 103 will also be designated the operating field camera 103. The second camera 103 may have a configuration and function similar to any of various known types of cameras typically installed in an operating room. For example, the second camera 103 may be provided with an auto exposure (AE) function that automatically adjusts the exposure, and an auto focus (AF) function that automatically adjusts the focus distance (i.e. a distance between the camera and a focus point of the camera), so that the state of surgery, particularly the operating site of the patient 203, may be captured appropriately.

The operating field camera 103 transmits information (operating field image information) about the medical image that the operating field camera 103 itself has taken (hereinafter also called a operating field image) to the control device 109 on a certain interval corresponding to the frame rate of the medical image, for example. Also, at this time, the operating field camera 103 associates operating field camera status information indicating the status of the operating field camera 103 with the operating field image information as metadata, and transmits the metadata together with the operating field image information to the control device 109. In the first embodiment, the operating field camera status information at least includes information about the focus distance adjusted by the AF function described above.

Note that in this specification, a camera like field of view camera 101 whose position and/or attitude are movable during surgery may also be designated a moving camera. Meanwhile a camera like the operating field camera 103 whose position and attitude are fixed may also be designated a fixed camera.

The display device 105, under control by the control device 109, displays an field of view image from the field of view camera 101 or an operating field image from the operating field camera 103. The control device 109 decides which medical image to display. Any of various known types of display devices, such as a liquid crystal display device or an electroluminescence (EL) display device, for example, may be applied as the display device 105.

The storage device 107, under control by the control device 109, saves field of view image information from the field of view camera 101 or operating field image information from the operating field camera 103, corresponding to what is displayed on the display device 105. At this point, the storage device 107 saves the image information together with metadata associated with the image information. Similarly to the medical image displayed on the display device 105, the control device 109 decides which image information to save. Any of various known types of devices capable of saving information may be used as the storage device 107, such as a magnetic storage device like a hard disk drive (HDD), a semiconductor storage device, an optical storage device, or a magneto-optical storage device.

The control device 109 centrally controls the image management functions in the system 1. Specifically, the control device 109 includes an image decision unit 111 as a function. The image decision unit 111 decides medical image to display on the display device 105 and image information to save in the storage device 107 (hereinafter collectively designated the medical image to adopt) from among the field of view image from the field of view camera 101 and the operating field image from the operating field camera 103. Note that the control device 109 may be a processor such as a central processing unit (CPU) or a digital signal processor (DSP), a control board on which a processor and a storage element such as memory are both mounted, a general information processing device such as a personal computer (PC) including an on-board processor, or the like, for example. As a result of the processor constituting the control device 109 executing computational processing in accordance with a certain program, the function of the image decision unit 111 may be realized.

In the first embodiment, the image decision unit 111 decides which medical image to adopt on the basis of at least one of the field of view camera status information transmitted from the field of view camera 101 and the operating field camera status information transmitted from the operating field camera 103. At this point, the image decision unit 111 decides the medical image including the operating site of the patient 203 to be observed from among the field of view image and the operating field image as the medical image to adopt.

Herein, the system 1 is provided with multiple imaging devices (the field of view camera 101 and the operating field camera 103), and medical images are taken during surgery by these multiple imaging devices. On the other hand, the purposes of taking these medical images in the first embodiment may be to share the state of the operating site during surgery with other medical staff by displaying images on the display device 105, to leave a record of the surgery by saving images to the storage device 107, to create educational materials for young doctors, and so on. Consequently, the medical images taken by these multiple imaging devices are preferably medical images of the operating site of the patient 203 (in other words, medical images that indicate how the surgeon 201 is performing various treatments on the operating site). By displaying on the display device 105 medical images that indicate how the surgeon 201 is performing various treatments on the operating site of the patient 203, medical staff in the operating room are able to share the current state of the operating site as well as the details of the treatment by the surgeon 201, and thereby realize smooth execution of surgery. Also, by saving to the storage device 107 medical images that indicate how the surgeon 201 is performing various treatments on the operating site of the patient 203, the medical images become a useful record when checking the state of the surgery at a later date.

However, depending on the status of the imaging devices during surgery, appropriate medical images may not necessarily be taken. For example, if the surgeon 201 is looking near-forward as illustrated in FIG. 1, or in other words, if the operating site of the patient 203 is not included in the field of view of the surgeon 201, the operating site will not be captured by the field of view camera 101. On the other hand, in this case, there is a high likelihood that the operating site is being captured by the operating field camera 103.

As another example, if the surgeon 201 is peering down at the operating site of the patient 203 as illustrated in FIG. 2, the operating site will be included in the field of view of the surgeon 201, and thus the operating site may be captured by the field of view camera 101. On the other hand, in this case, the head of the surgeon 201 becomes an obstruction, and there is a high likelihood that the operating site will not be captured by the operating field camera 103.

Consequently, if all of the field of view images and the operating field images that have been taken are displayed and saved, even unwanted medical images that do not include the operating site of the patient 203 will be displayed and saved, and the purposes described above are difficult to achieve favorably. Accordingly, in the first embodiment, as described earlier, the image decision unit 111 executes a process of deciding the medical image that more reliably depicts the operating site of the patient 203 from among the field of view image and the operating field image as the medical images to adopt. By this process, only the more appropriate medical images that include the operating site of the patient 203 during surgery are displayed and saved.

Specifically, in the system 1, with regard to the status of the field of view camera 101 and the status of the operating field camera 103, a condition for determining whether or not to decide an image as the medical image to adopt (hereinafter also called the image decision condition) is set in advance. For the image decision condition, a condition is set whereby the operating site of the patient 203 will be included in the captured image. The image decision unit 111 determines whether or not the image decision condition is satisfied on the basis of the field of view camera status information and/or the operating field camera status information. Subsequently, from among the field of view image and the operating field image, the image decision unit 111 decides, as the medical image to adopt, the medical image corresponding to the one for which the status of the field of view camera 101 or the status of the operating field camera 103 satisfies the image decision condition.

For example, the image decision condition for the status of the field of view camera 101 may be that the field of view camera 101 is tilted by a certain angle or more from the horizontal direction. The certain angle is set as a value indicating the visual field over a range of angles in which the operating site of the patient 203 may be included in the field of view of the surgeon 201, and may be set suitably in accordance with factors such as the height of the surgeon 201 and the positional relationship between the surgeon 201 and the patient 203. The image decision unit 111 determines whether or not the field of view camera 101 is tilted by the certain angle or more from the horizontal direction on the basis of information about the attitude of the field of view camera 101 included in the field of view camera status information, and if the field of view camera 101 is tilted by the certain angle or more, the image decision unit 111 decides to adopt the field of view image.

As another example, the image decision condition for the status of the operating field camera 103 may be that the focus distance of the operating field camera 103 is within a certain range. The certain range may be set suitably as a range whereby the focus point of the operating field camera 103 is roughly aligned with the operating site of the patient 203. Since the focus distance of the operating field camera 103 when the focus point of the operating field camera 103 is aligned with the operating site of the patient 203 is known from the positional relationship between the operating field camera 103 and the patient 203, it is possible to set such a certain range in advance. The image decision unit 111 determines whether or not the focus distance of the operating field camera 103 is within the certain range on the basis of information about the focus distance included in the operating field camera status information, and if the focus distance is within the certain range, the image decision unit 111 decides to adopt the operating field image.

Note that if the image decision condition for the status of the field of view camera 101 and the image decision condition for the status of the operating field camera 103 are both satisfied, the image decision unit 111 may suitably select the image depicting the operating site of the patient 203 more reliably from among the field of view image and the operating field image. For example, in accordance with the performance of the field of view camera 101 and the operating field camera 103, the properties of the operating site, and the like, a priority ranking of the field of view image and the operating field image may be set in advance from the perspective of capturing the operating site more reliably, and if the image decision condition for the status of the field of view camera 101 and the image decision condition for the status of the operating field camera 103 are both satisfied, the image decision unit 111 may decide the medical image to adopt in accordance with the priority ranking. Alternatively, for example, the degree to which the image decision condition for the status of the field of view camera 101 is satisfied and the degree to which the image decision condition for the status of the operating field camera 103 is satisfied may be quantitatively evaluated using a suitable evaluation function, and if the image decision condition for the status of the field of view camera 101 and the image decision condition for the status of the operating field camera 103 are both satisfied, the image decision unit 111 may decide the medical image corresponding to the greater degree as the medical image to adopt.

Conversely, if neither the image decision condition for the status of the field of view camera 101 nor the image decision condition for the status of the operating field camera 103 is satisfied, the image decision unit 111 may also adopt neither the field of view image nor the operating field image. This is because in this case, it is conceivable that the operating site of the patient 203 is not depicted clearly in either the field of view image or the operating field image, and thus there is little or no significance in displaying and saving such medical images. In this case, nothing is displayed on the display device 105 and nothing is saved in the storage device 107 while neither the image decision condition for the status of the field of view camera 101 nor the image decision condition for the status of the operating field camera 103 is satisfied.

After deciding the medical image to adopt, the image decision unit 111 controls the operation of the display device 105 to display the decided medical image on the display device 105. Additionally, the image decision unit 111 controls the operation of the storage device 107 to save the decided medical image in the storage device 107. At this point, the image decision unit 111 also saves metadata associated with the decided medical image (that is, field of view camera status information if the decided medical image is the field of view image, or operating field camera status information if the decided medical image is the operating field image) together with the medical image.

The above thus describes a configuration of the system 1 according to the first embodiment. Note that although FIGS. 1 to 3 illustrate the display device 105, the storage device 107, and the control device 109 as respectively separate devices, the configuration of the system 1 is not limited to such an example. It is sufficient to configure the system 1 by providing one or multiple devices having similar functions as these devices, and the specific device configuration of the system 1 may be decided arbitrarily. For example, these devices may also be configured as a unified device. In this case, the control device 109 may be provided with a display unit having functions similar to the display device 105, and a storage unit having similar functions as the storage device 107.

At this point, as exemplified by Patent Literature 1, systems that manage medical images taken during surgery are already being developed. However, as described earlier, since the technology described in Patent Literature 1 manages medical images by using the results of analyzing the taken medical images, when the image analysis cannot be conducted smoothly, such as when the analysis of medical images is time-consuming or when the medical images are not clear, there is a risk that appropriate management of medical images may not be available.

In contrast, according to the first embodiment, as described above, the medical image to adopt is decided without using the results of image analysis, on the basis of imaging device status information that indicates the status of the imaging device (field of view camera status information and/or operating field camera status information). Consequently, the trouble that may occur when using the results of image analysis may be avoided, making it possible to manage medical images more appropriately. As a result, the work of editing the obtained medical images after surgery becomes unnecessary, and the burden on the medical staff is reduced. Additionally, since only the significant medical images are saved automatically, the amount of data saved in the storage device 107 may be reduced, and costs may be lowered.

Note that in the first embodiment, the system 1 includes the field of view camera 101. Since the field of view camera 101 is able to recreate the field of view of the surgeon 201 actually performing surgery, images taken by the field of view camera 101 may be extremely significant as medical images indicating the state of surgery. Conversely, since the field of view camera 101 is a moving camera, the range taken by the camera is expected to change frequency during surgery, and compared to a fixed camera, there is a high likelihood that an appropriate medical image including the operating site may not be taken. Consequently, in the case of capturing the state of surgery with multiple imaging devices including a moving camera like the field of view camera 101, it is highly important to decide appropriately the medical image to adopt from among the taken medical images. According to the system 1 according to the first embodiment, as described above, it is possible to manage medical images more appropriately, and thus the system 1 exhibits more advantageous effects when the medical images taken during surgery include medical images taken by a moving camera.

In addition, one of the characteristics of a moving camera is that the position and the attitude of the moving camera may change. As a result of such a characteristic, trouble may also occur in which an appropriate medical image that includes the operating site as described above may not necessarily be taken. In contrast, in the system 1, the fulfillment of the image decision condition is determined and the medical image to adopt is decided on the basis of information about the attitude of the moving camera, that is, the field of view camera 101. In other words, an image decision condition taking the characteristics of the moving camera into account is set, and the medical image to adopt is decided on the basis of the image decision condition. In this way, by setting an appropriate image decision condition by which the above-described trouble occurring because of such characteristics may be resolved more effectively, it becomes possible to determine more appropriately whether or not to decide an image captured by the moving camera as the medical image to adopt.

Note that in the above description, the image decision condition regarding the status of the field of view camera 101 relates to the attitude of the field of view camera 101, and correspondingly, the field of view camera status information at least includes information about the attitude of the field of view camera 101, but the first embodiment is not limited to such an example. The field of view camera status information may also include other information related to the status of the field of view camera 101. For example, the field of view camera status information may include information about factors such as the position and the acceleration of the field of view camera 101. This information may be acquired by providing the field of view camera 101 with a position sensor or an acceleration sensor, for example. In this case, a condition whereby the field of view camera 101 is anticipated to be capturing the operating site of the patient 203, such as the field of view camera 101 being positioned in a certain range directly above the operating site, for example, may be set appropriately as the image decision condition.

Also, in the above description, the image decision condition regarding the status of the operating field camera 103 relates to the attitude of the operating field camera 103, and correspondingly, the operating field camera status information at least includes information about the focus distance of the operating field camera 103, but the first embodiment is not limited to such an example. The operating field camera status information may also include other information related to the status of the operating field camera 103. For example, the operating field camera status information may include information about the exposure value of the operating field camera 103. Such information may be acquired as the exposure value adjusted by the AE function provided in the operating field camera 103. In this case, for example, the exposure value of the operating field camera 103 being within a certain range may be set as the image decision condition. The certain range is appropriately set as a range of exposure values which are anticipated when the operating field camera 103 is suitably capturing the operating site, for example.

1-2. Control Method

A processing sequence of a control method of the system 1 according to the first embodiment described above will be described with reference to FIG. 4. FIG. 4 is a flowchart illustrating an example of a processing sequence of a control method according to the first embodiment. Note that each process illustrated in FIG. 4 corresponds to a process executed by the control device 109 illustrated in FIGS. 1 to 3. As a result of the processor constituting the control device 109 operating in accordance with a certain program, the respective processes illustrated in FIG. 4 are executed. Since the details of each process illustrated in FIG. 4 have already been described earlier in the description of the functions of the control device 109, in the following description of the processing sequence of the control method according to the first embodiment, an overview of each process will be described briefly, and detailed description will be reduced or omitted.

Referring to FIG. 4, in the control method according to the first embodiment, first, field of view image information and field of view camera status information is acquired from the field of view camera 101 (step S101). The process in step S101 corresponds to the process in which field of view image information and field of view camera status information is transmitted from the field of view camera 101 illustrated in FIGS. 1 to 3 to the control device 109.

Next, operating field image information and operating field camera status information is acquired from the operating field camera 103 (step S103). The process in step S103 corresponds to the process in which operating field image information and operating field camera status information is transmitted from the operating field camera 103 illustrated in FIGS. 1 to 3 to the control device 109. Note that in FIG. 4, the process in step S101 and the process in step S103 are described as being conducted sequentially for the sake of convenience, but during actual surgery, the process in step S101 and the process in step S103 may be executed in parallel on a certain interval for each (for example, a certain interval corresponding to the respective frame rate of the field of view image and the operating field image).

Next, on the basis of the field of view camera status information and/or the operating field camera status information, the medical image to adopt from is decided from among the field of view image and the operating field image (step S105). The process in step S105 corresponds to the process executed by the image decision unit 111 of the control device 109 illustrated in FIGS. 1 to 3.

Subsequently, the decided medical image is displayed on the display device 105 while also being saved to the storage device 107 (step S107). The process in step S107 corresponds to the process executed by the image decision unit 111 of the control device 109 illustrated in FIGS. 1 to 3 to respectively control the operation of the display device 105 and the storage device 107.

The above thus describes a processing sequence of a control method according to the first embodiment.

2. Second Embodiment

A second embodiment of the present disclosure will now be described. Note that in the systems according to the second to fourth embodiments described hereinafter, the types of imaging devices installed are changed with respect to the system 1 according to the first embodiment described above, and correspondingly, the image decision unit 111 corresponds to one in which the image decision condition which acts as the basis for deciding the medical image to adopt is changed. Other items are mostly similar to the first embodiment. Consequently, in the following description of the second to fourth embodiments, the differences from the first embodiment will be described primarily, whereas detailed description will be reduced or omitted for items that overlap.

2-1. Configuration of System

A configuration of a system according to a second embodiment will be described with reference to FIGS. 5 and 6. FIG. 5 is a diagram illustrating a diagrammatic configuration of a system according to the second embodiment. FIG. 6 is a block diagram illustrating a functional configuration of a system according to the second embodiment. FIG. 5 illustrates a situation in which surgery is being performed on a operating site 209 of a patient, and the state of the surgery is being captured using a system 2 according to the second embodiment.

Referring to FIGS. 5 and 6, the system 2 according to the second embodiment is provided with multiple (in the illustrated example, three) moving cameras 121, a position sensor 123 that detects the positions of the multiple moving cameras 121, a display device 105 which is installed inside the operating room and which displays one of the medical images from among the medical images respectively taken by the multiple moving cameras 121, a storage device 107 that saves image information corresponding to a medical image displayed on the display device 105, and a control device 109 that decides which medical image to display on the display device 105 and which image information to save in the storage device 107. In this way, the system 2 corresponds to the system 1 according to the first embodiment described above being provided with multiple moving cameras 121 instead of the field of view camera 101 and the operating field camera 103.

For example, the moving cameras 121 are respectively attached to the head of the surgeon, the head of an assistant, and a treatment tool used in surgery (such as forceps, for example). The moving cameras 121 attached to the head of the surgeon and the head of the assistant function as field of view cameras that capture the field of view of the surgeon and the assistant, respectively, similarly to the field of view camera 101 in the system 1 according to the first embodiment. The moving camera 121 attached to the treatment tool is able to capture the operating site 209 when the treatment tool is brought close to the operating site 209. However, the objects to which the moving cameras 121 are attached are not limited to such an example, and in the second embodiment, the moving cameras 121 may be attached to any of various types of objects which may be pointed at the operating site 209 during surgery. Also, each moving camera 121 may be provided with an AF function.

Each moving camera 121 transmits information (moving camera image information) about the medical image that the moving camera itself has taken (hereinafter also called a moving camera image) to the control device 109 on a certain interval corresponding to the frame rate of the medical image, for example. Also, at this time, each moving camera 121 associates moving camera status information indicating the status of the moving camera itself with the moving camera image information as metadata, and transmits the metadata together with the moving camera image information to the control device 109. In the second embodiment, the moving camera status information at least includes information about the focus distance adjusted by the AF function described above.

A marker 125 for detecting position is attached to each moving camera 121, and the position sensor 123 detects the position of these markers 125 to thereby detect the position of each moving camera. For example, the position sensor 123 is a magnetic sensor, and the marker 125 is a magnetic marker. Alternatively, for example, the position sensor 123 is a camera capable of acquiring depth information, such as a stereo camera, and the position sensor 123 detects the markers 125 from a taken image to thereby detect the position of each moving camera 121. The position sensor 123 transmits the detected position information about each moving camera 121 to the control device 109. The interval on which the position sensor 123 transmits the position information to the control device 109 may be comparable to the interval on which the moving camera 121 transmits moving camera image information to the control device 109, for example. Note that it is sufficient for the position sensor 123 to be able to detect the three-dimensional position of each moving camera 121, and any of various known types of sensors may be used as the position sensor 123.

The position information about each moving camera 121 detected by the position sensor 123 may be thought of as one type of moving camera status information indicating the status of each moving camera 121. In this way, in the second embodiment, moving camera status information is acquired by the moving camera 121 and the separately provided position sensor 123.

Similarly to the first embodiment, the control device 109 includes an image decision unit 111 as a function. The image decision unit 111 decides one medical image to display on the display device 105 and one medical image to save in the storage device 107 (in other words, one medical image to adopt) from among moving camera images from the multiple moving cameras 121.

The image decision unit 111 decides which medical image to adopt on the basis of the moving camera status information transmitted from the moving cameras 121 and the position sensor 123. At this point, in the second embodiment, similarly to the first embodiment, the image decision unit 111 decides a medical image including the operating site 209 to be observed from among the moving camera images from the multiple moving cameras 121 as the medical image to adopt.

Specifically, in the system 2, with regard to the status of the moving cameras 121, a condition by which the operating site 209 is included in a captured image is set in advance as an image decision condition. The image decision unit 111 determines whether or not the image decision condition is satisfied on the basis of the moving camera status information. Subsequently, from among the multiple moving camera images, the image decision unit 111 decides, as the medical image to adopt, the medical image corresponding to the one for which the status of the corresponding moving camera 121 satisfies the image decision condition.

For example, the image decision condition for the status of a moving camera 121 is that the focus point of the moving camera 121 is aligned with the operating site 209. The position of the operating site 209 of the patient inside the operating room is already known. Since position information about each moving camera 121 is transmitted as moving camera status information from the position sensor 123 to the control device 109, the image decision unit 111 is able to use such position information as a basis for respectively computing the positional relationship between each moving camera 121 and the operating site 209. Also, information about the focus distance is transmitted as moving camera status information from each moving camera 121 to the control device 109. Consequently, the image decision unit 111 is able to determine whether or not the focus point of each moving camera 121 is aligned with the operating site 209 from the position of the operating site 209 inside the operating room, the computed positional relationship, and the information about the focus distance. In other words, the image decision unit 111 is able to determined whether or not the status of each moving camera 121 satisfies the above image decision condition.

If the determination result indicates that the status of any moving camera 121 satisfies the above operating site inclusion condition, the image decision unit 111 decides, as the medical image to adopt, the moving camera image taken by the moving camera 121 that satisfies the image decision condition. For example, in the example illustrated in FIG. 5, for a camera pointing in a different direction than the direction in which the operating site 209 exists, like the moving camera 121 position in the upper-right as viewed in the diagram, or for a camera for which an obstruction 207 (such as another medical staff member or any of various types of tools used in surgery, for example) exists between the moving camera 121 and the operating site 209 in the direction of taking an image of the operating site 209, like the moving camera 121 positioned in the lower-right as viewed in the diagram, it is determined that the focus point is not aligned with the operating site 209, or in other words, the image decision condition is not satisfied. Meanwhile, for a camera pointing in the direction in which the operating site 209 exists, and for which the focus point is considered to be aligned with the operating site 209 based on the distance between the moving camera 121 and the operating site 209, and the focus distance of the moving camera 121, like the moving camera 121 positioned on the left side as viewed in the diagram, it is determined that the moving camera 121 satisfies the image decision condition. Consequently, the moving camera image taken by that moving camera 121 is decided as the medical image to adopt.

Note that if the image decision condition is satisfied with regard to the status of multiple moving cameras 121 at the same time, the image decision unit 111 may suitably select the image depicting the operating site 209 more reliably from among the multiple corresponding moving camera images. For example, in accordance with the performance of each moving camera 121, the properties of the operating site, and the like, a priority ranking of the moving cameras 121 may be set in advance from the perspective of capturing the operating site more reliably, and if the image decision condition is satisfied with regard to the status of multiple moving cameras 121 at the same time, the image decision unit 111 may decide the medical image to adopt in accordance with the priority ranking. Alternatively, for example, the degree to which the image decision condition for the status of each moving camera 121 is satisfied may be quantitatively evaluated using a suitable evaluation function, and if the image decision condition is satisfied with regard to the status of multiple moving cameras 121 at the same time, the image decision unit 111 may decide the medical image corresponding to the greater degree as the medical image to adopt.

Conversely, if the image decision condition is not satisfied with regard to the status of any of the multiple moving cameras 121, the image decision unit 111 may also adopt none of the moving camera images. This is because in this case, it is conceivable that the operating site 209 is not depicted clearly in any of the moving camera images, and thus there is little or no significance in displaying and saving such medical images.

After deciding the medical image to adopt, the image decision unit 111 controls the operation of the display device 105 to display the decided medical image on the display device 105. Additionally, the image decision unit 111 controls the operation of the storage device 107 to save the decided medical image in the storage device 107. At this point, the image decision unit 111 also saves metadata associated with the decided medical image (that is, the moving camera status information for the moving camera 121 that took the decided medical image) together with the medical image.

The above thus describes a configuration of the system 2 according to the second embodiment. Note that in the above description, the moving camera status information includes position information about the moving camera 121 and information about the focus distance, but the second embodiment is not limited to such an example. It is sufficient for the moving camera status information to include information that may contribute to the determination of the image decision condition stipulating that the focus point is aligned with the operating site 209, and thus the above information may not necessarily be included, and any of various other types of information may also be included. For example, information about the attitude of each moving camera 121 may indicate the direction in which each moving camera is pointing, and thus may contribute to the determination of the image decision condition. Consequently, each moving camera 121 may be provided with an attitude sensor, and information about the attitude of each moving camera 121 detected by the attitude sensor may also be included in the moving camera status information.

2-2. Control Method

A processing sequence of a control method in the system 2 according to the second embodiment described above will be described with reference to FIG. 7. FIG. 7 is a flowchart illustrating an example of a processing sequence of a control method according to the second embodiment. Note that each process illustrated in FIG. 7 corresponds to a process executed by the control device 109 illustrated in FIGS. 5 and 6. As a result of the processor constituting the control device 109 operating in accordance with a certain program, the respective processes illustrated in FIG. 7 are executed. Since the details of each process illustrated in FIG. 7 have already been described earlier in the description of the functions of the control device 109, in the following description of the processing sequence of the control method according to the second embodiment, an overview of each process will be described briefly, and detailed description will be reduced or omitted.

Referring to FIG. 7, in the control method according to the second embodiment, first, moving camera image information and moving camera status information is acquired from the moving cameras 121 (step S201). The process in step S201 corresponds to the process in which moving camera image information and moving camera status information is transmitted from each moving camera 121 illustrated in FIGS. 5 and 6 to the control device 109.

Next, moving camera status information (specifically, position information about each moving camera 121) is acquired from the position sensor 123 (step S203). The process in step S203 corresponds to the process in which position information about each moving camera 121 is transmitted as moving camera status information from the position sensor 123 illustrated in FIGS. 5 and 6 to the control device 109. Note that in FIG. 7, the process in step S201 and the process in step S203 are described as being conducted sequentially for the sake of convenience, but during actual surgery, the process in step S201 and the process in step S203 may be executed in parallel on a certain interval for each (for example, a certain interval corresponding to the frame rate of the moving camera image).

Next, on the basis of the moving camera status information, the medical image to adopt is decided from among the multiple moving camera images (step S205). The process in step S205 corresponds to the process executed by the image decision unit 111 of the control device 109 illustrated in FIGS. 5 and 6.

Subsequently, the decided medical image is displayed on the display device 105 while also being saved to the storage device 107 (step S207). The process in step S207 corresponds to the process executed by the image decision unit 111 of the control device 109 illustrated in FIGS. 5 and 6 to respectively control the operation of the display device 105 and the storage device 107.

The above thus describes a processing sequence of a control method according to the second embodiment.

3. Third Embodiment 3-1. Configuration of System

A configuration of a system according to a third embodiment will be described with reference to FIGS. 8 and 9. FIG. 8 is a diagram illustrating a diagrammatic configuration of a system according to the third embodiment. FIG. 9 is a block diagram illustrating a functional configuration of a system according to the third embodiment. FIG. 8 illustrates a situation in which surgery is being performed on a operating site 209 of a patient, and the state of the surgery is being captured using a system 3 according to the third embodiment.

Referring to FIGS. 8 and 9, the system 3 according to the third embodiment is provided with a microscope device 5301 for enlarged observation of the operating site 209 of the patient, an endoscope device 5401 for observing the interior or the underside of the operating site 209 of the patient, a display device 105 which is installed inside the operating room and which displays at least one medical image from among the medical images respectively taken by the microscope device 5301 and the endoscope device 5401, a storage device 107 that saves image information corresponding to a medical image displayed on the display device 105, and a control device 109 that decides which medical image to display on the display device 105 and which image information to save in the storage device 107. In this way, the system 3 corresponds to the system 1 according to the first embodiment described above being provided with the microscope device 5301 and the endoscope device 5401 instead of the field of view camera 101 and the operating field camera 103. In other words, the system 3 is applied favorably to surgery that uses the microscope device 5301 and the endoscope device 5401 jointly.

The microscope device 5301 includes a microscope unit 5303 for enlarged observation of the operating site 209 of the patient to be observed, an arm unit 5309 that supports the microscope unit 5303 on the leading end, a base unit 5315 that supports the arm unit 5309 on the base end, and a microscope control device 5317 that controls the operation of the microscope device 5301. In the microscope device 5301, the position and the attitude of the microscope unit 5303 may be controlled arbitrarily by the arm unit 5309, within the movable range of the arm unit 5309. In other words, the microscope device 5301 is configured to allow movement of the microscope unit 5303 which includes the imaging function of the device, and thus may be considered to be a type of moving camera. By supporting the microscope unit 5303 with the arm unit 5309, the positioning of the microscope unit 5303 may be conducted with high precision, while in addition, the position and the attitude may be maintained in a desired state more reliably, thereby making it possible to obtain captured images more consistently.

The microscope unit 5303 is made up of an approximately cylindrical barrel unit 5305, an imaging unit (not illustrated) provided inside the barrel unit 5305, and an operating unit 5307 provided in a partial region on the outer circumference of the barrel unit 5305. The microscope unit 5303 is an electronic imaging microscope unit (also known as a video microscope unit) that images a captured image electronically with the imaging unit.

The aperture on the bottom end of the barrel unit 5305 is provided with a cover glass that protects the imaging unit inside. Light from the observation target (hereinafter also called observation light) passes through the cover glass and is incident on the imaging unit inside the barrel unit 5305. Note that a light source made up of a light-emitting diode (LED) or the like, for example, may also be provided inside the barrel unit 5305, and during imaging, light may be radiated from the light source onto the observation target through the cover glass.

The imaging unit is made up of an optical system that condenses observation light, and an image sensor that senses the observation light condensed by the optical system. The optical system is made up of a combination of multiple lenses, including a zoom lens and a focus lens, the optical characteristics of which are adjusted so that an image of the observation light is formed on the light-sensitive face of the image sensor. The image sensor senses and photoelectrically converts the observation light to thereby generate a signal corresponding to the observation light, or in other words, an image signal corresponding to the observed image. A sensor capable of color photography including a Bayer array, for example, is used as the image sensor. The image sensor may be any of various known types of image sensors, such as a complementary metal-oxide-semiconductor (CMOS) image sensor or a charge-coupled device (CCD) image sensor. The image signal generated by the image sensor is transmitted to the microscope control device 5317 as RAW data. At this point, the transmission of the image signal may be conducted favorably by optical communication. This is because at the surgery venue, the surgeon performs surgery while observing the state of the affected area via the captured image, and thus for safer and more reliable surgery, there is demand for the moving image of the operating site to be displayed as close to real-time as possible. Transmitting the image signal by optical communication makes it possible to display the captured image with low latency.

Note that the image unit may also include a driving mechanism that moves the zoom lens and the focus lens of the optical system along the optical axis. By suitably moving the zoom lens and the focus lens with the driving mechanism, the magnification factor of the captured image and the focus distance during imaging may be adjusted. By suitably driving the optical system, the imaging unit is provided with a function of adjusting the focus distance automatically (in other words, an AF function). Also, the imaging unit may be provided with any of various types of functions typically provided in electronic imaging microscope units, such as an AE function.

In addition, the imaging unit may be configured as a so-called one-chip imaging unit that includes a single image sensor, or as a so-called multi-chip imaging unit that includes multiple image sensors. If the imaging unit has a multi-chip configuration, image signals corresponding to R, G, and B are generated by respective image sensors, for example, and a color image may be obtained by combining these image signals. Alternatively, the imaging unit may be configured to include a pair of image sensors for respectively acquiring image signals for the right eye and the left eye corresponding to stereoscopic vision (3D display). By presenting a 3D display, the surgeon becomes able to grasp the depth of biological tissue in the operating site more accurately. Note that if the imaging unit has a multi-chip configuration, the optical system is provided with multiple subsystems corresponding to each of the image sensors.

The operating unit 5307 is made up of elements such as a directional lever or switches, for example, and is an input unit that accepts operating input from a user (a medical staff member such as the surgeon who uses the system 3 as well as the microscope device 5301 and the endoscope device 5401). For example, via the operating unit 5307, the user is able to input an instruction to change the magnification factor of the observation target and the focus distance to the observation target. By having the driving mechanism of the imaging unit suitably drive the zoom lens and the focus lens in accordance with the instruction, the magnification factor and the focus distance may be adjusted. As another example, via the operating unit 5307, the user is able to input an instruction to toggle the operating mode of the arm unit 5309 (an all-free mode and a locked mode described later). Note that when the user wants to move the microscope unit 5303, it is anticipated that the user moves the microscope unit 5303 by gripping and holding the barrel unit 5305. Consequently, the operating unit 5307 preferably is provided at a position that allows easy operation with the fingers while the user is gripping the barrel unit 5305, to thereby allow the user to operate the operating unit 5307 even while moving the barrel unit 5305.

The arm unit 5309 is configured as a result of multiple links (a first link 5313*a* to a sixth link 5313*f*) being rotatably joined to each other by multiple joint units (a first joint unit 5311*a* to a sixth joint unit 53110.

The first joint unit 5311*a* has an approximately cylindrical shape, and on the leading end (bottom end) thereof supports the top end of the barrel unit 5305 of the microscope unit 5303, so as to allow rotation about a rotation axis (first axis $O_1$) parallel to the central axis of the barrel unit 5305. Herein, the first joint unit 5311*a* may be configured so that the first axis $O_1$ is aligned with the optical axis of the microscope unit 5303. Consequently, rotating the microscope unit 5303 about the first axis $O_1$ makes it possible to change the field of view as though rotating the captured image.

The first link 5313*a* securely supports the first joint unit 5311*a* on the leading end thereof. Specifically, the first link 5313*a* is an approximately L-shaped rod-like member, the leading edge of which extends in a direction orthogonal to the first axis $O_1$, while also being connected to the first joint unit 5311*a* so that the end of that edge abuts the top end on the outer circumference of the first joint unit 5311*a*. The second joint unit 5311*b* is connected to the end of the base edge of the approximate L-shape of the first link 5313*a*.

The second joint unit 5311*b* has an approximately cylindrical shape, and on the leading end thereof supports the base end of the first link 5313*a*, so as to allow rotation about a rotation axis (second axis $O_2$) orthogonal to the first axis $O_1$. The leading end of the second link 5313*b* is securely connected to the base end of the second joint unit 5311*b*.

The second link 5313*b* is an approximately L-shaped rod-like member, the leading edge of which extends in a direction orthogonal to the second axis $O_2$, while the end of that edge is securely connected to the base end of the second joint unit 5311*b*. The third joint unit 5311*c* is connected to the base edge of the approximate L-shape of the second link 5313*b*.

The third joint unit 5311*c* has an approximately cylindrical shape, and on the leading end thereof supports the base end of the second link 5313*b*, so as to allow rotation about a rotation axis (third axis $O_3$) orthogonal to both the first axis $O_1$ and the second axis $O_2$. The leading end of the third link 5313*c* is securely connected to the base end of the third joint unit 5311*c*. By rotating the configuration on the leading-end side, including the microscope unit 5303, about the second axis $O_2$ and the third axis $O_3$, the microscope unit 5303 may be moved to change the position of the microscope unit 5303 on the horizontal plane. In other words, controlling the rotation about the second axis $O_2$ and the third axis $O_3$ makes it possible to move the field of view of the captured image on a flat plane.

The third link 5313c is configured to have an approximately cylindrical shape on the leading end side, and on the leading end of the cylindrical shape, the base end of the third joint unit 5311c is securely connected so that both have approximately the same central axis. The base end side of the third link 5313c has a rectangular column shape, and the fourth joint unit 5311d is connected to the end thereof.

The fourth joint unit 5311d has an approximately cylindrical shape, and on the leading end thereof supports the base end of the third link 5313c, so as to allow rotation about a rotation axis (fourth axis $O_4$) orthogonal to the third axis $O_3$. The leading end of the fourth link 5313d is securely connected to the base end of the fourth joint unit 5311d.

The fourth link 5313d is a rod-like member that extends approximately linearly in a direction orthogonal to the fourth axis $O_4$, while also being securely connected to the fourth joint unit 5311d so that the leading end abuts the side face of the approximately cylindrical shape of the fourth joint unit 5311d. The fifth joint unit 5311e is connected to the base end of the fourth link 5313d.

The fifth joint unit 5311e has an approximately cylindrical shape, and on the leading end side thereof supports the base end of the fourth link 5313d, so as to allow rotation about a rotation axis (fifth axis $O_5$) parallel to the fourth axis $O_4$. The leading end of the fifth link 5313e is securely connected to the base end of the fifth joint unit 5311e. The fourth axis $O_4$ and the fifth axis $O_5$ are rotation axes enabling the microscope unit 5303 to be moved in the vertical direction. By rotating the configuration on the leading-end side, including the microscope unit 5303, about the fourth axis $O_4$ and the fifth axis $O_5$, the height of the microscope unit 5303, or in other words the distance between the microscope unit 5303 and the observation target, may be adjusted.

The fifth link 5313e is made up of a combination of a first member having an approximate L-shape with one edge extending in the vertical direction while the other edge extends in the horizontal direction, and a rod-like second member that extends vertically downward from the part of the first member that extends in the horizontal direction. The base end of the fifth joint unit 5311e is securely connected near the top end of the part of the first member that extends in the vertical direction of the fifth link 5313e. The sixth joint unit 5311f is connected to the base end (bottom end) of the second member of the fifth link 5313e.

The sixth joint unit 5311f has an approximately cylindrical shape, and on the leading end side thereof supports the base end of the fifth link 5313e, so as to allow rotation about a rotation axis (sixth axis $O_6$) parallel to the vertical direction. The leading end of the sixth link 5313f is securely connected to the base end of the sixth joint unit 5311f.

The sixth link 5313f is a rod-like member that extends in the vertical direction, with the base end securely connected to the top face of the base unit 5315.

The allowable rotation range of the first joint unit 5311a to the sixth unit 5311f is suitably set so that the microscope unit 5303 is capable of desired motion. Consequently, in the arm unit 5309 having the configuration described above, three degrees of translational freedom and three degrees of rotational freedom, for a total of six degrees of freedom, may be realized for the motion of the microscope unit 5303. In this way, by configuring the arm unit 5309 so that six degrees of freedom are realized for the motion of the microscope unit 5303, it becomes possible to freely control the position and the attitude of the microscope unit 5303 within the movable range of the arm unit 5309. Consequently, it becomes possible to observe a operating site from any angle, and surgery may be executed more smoothly.

Note that the configuration of the arm unit 5309 illustrated in the diagram is merely one example, and factors such as the number and the shapes (lengths) of the links constituting the arm unit 5309, as well as the number and arrangement of the joint units and the directions of the rotation axes may be designed suitably so that the desired degrees of freedom may be realized. For example, as described above, to move the microscope unit 5303 freely, the arm unit 5309 preferably is configured to have six degrees of freedom, but the arm unit 5309 may also be configured to have more degrees of freedom (in other words, redundant degrees of freedom). When redundant degrees of freedom exist, in the arm unit 5309, it becomes possible to change the attitude of the arm unit 5309 while keeping the position and the attitude of the microscope unit 5303 in a locked state. Consequently, control that is more convenient to the user, such as control of the attitude of the arm unit 5309 so that the arm unit 5309 does not interfere with the field of view of a user looking at the display device 105, particularly the surgeon, for example, may be realized.

Herein, the first joint unit 5311a to the sixth joint unit 5311f may be provided with actuators equipped with a driving mechanism such as a motor, an encoder that detects the rotation angle in each joint unit, and the like. In addition, by having the microscope control device 5317 suitable control the driving of each actuator provided for the first joint unit 5311a to the sixth joint unit 5311f, the attitude of the arm unit 5309, or in other words the position and the attitude of the microscope unit 5303, may be controlled. Specifically, the microscope control device 5317 is able to ascertain the current attitude of the arm unit 5309 as well as the current position and attitude of the microscope unit 5303, on the basis of information about the rotation angle of each joint unit detected by the encoder. The microscope control device 5317 uses the ascertained information to compute a control value for each joint unit (such as a rotation angle or a generated torque, for example) so that movement of the microscope unit 5303 corresponding to operation input from the user is realized. Note that at this point, the method by which the microscope control device 5317 controls the arm unit 5309 is not limited, and any of various known control methods, such as force control or position control, may be applied.

For example, by having the surgeon perform suitable operation input via an input device (not illustrated), the driving of the arm unit 5309 may be suitably controlled by the microscope control device 5317 in accordance with the operation input, and the position and the attitude of the microscope unit 5303 may be controlled. By such control, after moving the microscope unit 5303 from an arbitrary position to an arbitrary position, the microscope unit 5303 may be supported securely at the new position. Note that with regard to the input device, in consideration of the surgeon's convenience, a device enabling operation even while the surgeon is holding surgical tools in his or her hands, such as a footswitch, for example, is preferably applied. Also, non-contact operation input may also be performed on the basis of gesture detection or line-of-sight detection using wearable device or a camera provided inside the operating room. Consequently, even a user belonging to a clean area becomes able to operate equipment belonging to an unclean area with a greater degree of freedom. Alternatively, the arm unit 5309 may be operated by what is called a master-slave method. In this case, the arm unit 5309 may be operated remotely by a user via an input device installed in a location separate from the operating room.

Also, if force control is applied, what is called power-assist control may also be conducted, in which external force is received from a user, and the actuators of the first joint unit 5311*a* to the sixth joint unit 5311*f* are driven so that the arm unit 5309 moves smoothly in response to the external force. As a result, when the user grasps the microscope unit 5303 to move the position directly, the microscope unit 5303 may be moved with comparatively light force. Consequently, it becomes possible to move the microscope unit 5303 more intuitively with a simpler operation, and user convenience may be improved.

In addition, the driving of the arm unit 5309 may be controlled so as to perform a pivot operation. Herein, a pivot operation refers to an operation of moving the microscope unit 5303 so that the optical axis of the microscope unit 5303 stays pointed at a certain point in space (hereinafter called the pivot point). A pivot operation makes it possible to observe the same observation position from various direction, thereby making more detailed observation of the affected area possible. Note that if the microscope unit 5303 is used with the focus distance in a locked state, the pivot operation is preferably performed so that the distance between the microscope unit 5303 and the pivot point remains constant. In this case, it is sufficient to adjust the distance between the microscope unit 5303 and the pivot point to the locked focus distance of the microscope unit 5303. As a result, the microscope unit 5303 moves over the face of a hemisphere centered on the pivot point and having a radius corresponding to the focus distance, and clear captured images are obtained even if the observation direction is changed. On the other hand, if the microscope unit 5303 is used while suitably changing the focus distance, the pivot operation may be performed with a variable distance between the microscope unit 5303 and the pivot point. In this case, the AF function provided in the microscope unit 5303 is used, and every time the distance between the microscope unit 5303 and the pivot point changes due to the pivot operation, the focus distance is adjusted automatically by the AF function. Alternatively, the microscope control device 5317 may compute the distance between the microscope unit 5303 and the pivot point on the basis of information about the rotation angle of each joint detected by the encoder, and automatically adjust the focus distance of the microscope unit 5303 on the basis of the computed result.

In addition, the first joint unit 5311*a* to the sixth joint unit 5311*f* may also be provided with brakes that restrain rotation. The operation of such brakes may be controlled by the microscope control device 5317. For example, when it is desirable to lock the position and the attitude of the microscope unit 5303, the microscope control device 5317 applies the brake on each joint unit. As a result, the attitude of the arm unit 5309, or in other words the position and the attitude of the microscope unit 5303, may be locked without driving the actuators, and power consumption may be reduced. When it is desirable to move the position and the attitude of the microscope unit 5303, it is sufficient for the microscope control device 5317 to release the brake on each joint unit and drive the actuators in accordance with a certain control method.

Such a brake operation may be performed in response to operation input performed by a user via the operating unit 5307 described above. When the user wants to move the position and the attitude of the microscope unit 5303, the user operates the operating unit 5307 to release the brake on each joint unit. As a result, the operating mode of the arm unit 5309 switches to a mode allowing each joint unit to be rotated freely (all-free mode). Meanwhile, when the user wants to lock the position and the attitude of the microscope unit 5303, the user operates the operating unit 5307 to apply the brake on each joint unit. As a result, the operating mode of the arm unit 5309 switches to a mode in which the rotation of each joint unit is restrained (locked mode).

The microscope control device 5317 controls the operation of the microscope device 5301. For example, the microscope control device 5317 controls the driving of the arm unit 5309 by causing the actuators of the first joint unit 5311*a* to the sixth joint unit 5311*f* to operate in accordance with a certain control method. As another example, the microscope control device 5317 changes the operating mode of the arm unit 5309 by controlling the operation of the brakes of the first joint unit 5311*a* to the sixth joint unit 5311*f*. As another example, the microscope control device 5317 performs various types of signal processing on an image signal acquired by the imaging unit of the microscope unit 5303, and thereby generates image data for display. In other words, the microscope control device 5317 includes the function of a camera control unit (CCU). For the signal processing, any of various known types of signal processing, such as a development process (demosaicing process), an image quality-improving process (such as a band enhancement process, a super-resolution process, a noise reduction (NR) process, and/or a shake correction process), and/or an enlargement process (that is, a digital zoom process), may be performed.

Note that the communication between the microscope control device 5317 and the microscope unit 5303, as well as the communication between the microscope control device 5317 and the first joint unit 5311*a* to the sixth joint unit 5311*f*, may be wired communication or wireless communication. In the case of wired communication, communication using electrical signals may be conducted, or optical communication may be conducted. In this case, the transmission cable used for wired communication may be configured as an electrical signal cable, optical fiber, or a composite cable of the two, in accordance with the communication method. Meanwhile, in the case of wireless communication, it is no longer necessary to lay down a transmission cable inside the operating room, and thus a situation in which the movement of medical staff inside the operating room is impeded by such a transmission cable may be resolved.

The microscope control device 5317 transmits information (microscope image information) about the generated image data for display, or in other words a medical image taken by the microscope unit 5303 (hereinafter also called a microscope image), to the control device 109 at a certain interval corresponding to the frame rate of the medical image, for example. Also, at this point, the microscope control device 5317 associates microscope device status information indicating the status of the microscope device 5301 (more specifically, the status of the microscope unit 5303) with the microscope image information as metadata, and transmits the metadata together with the microscope image information to the control device 109. In the third embodiment, the microscope device status information at least includes information about the current position and attitude of the microscope unit 5303 obtained to control the operation of the arm unit 5309, and information about the focus distance of the microscope unit 5303 adjusted by the AF function.

The microscope control device 5317 may be a processor such as a central processing unit (CPU) or a graphics processing unit (GPU), a control board on which a processor and a storage element such as memory are both mounted, or the like. As a result of the processor of the microscope control device 5317 operating in accordance with a certain program, the various functions described above may be realized. Note that in the example illustrated in the diagram, the microscope control device 5317 is provides as a separate device from the main body of the microscope device 5301 (the microscope unit 5303, the arm unit 5309, and the base unit 5315), but the microscope control device 5317 may also be unified with the microscope device 5301, such as by being installed inside the base unit 5315 of the microscope device 5301, for example. Alternatively, the microscope control device 5317 may be made up of multiple devices. For example, by disposing a control board or the like in the microscope unit 5303 and each of the first joint unit 5311*a* to the sixth joint unit 5311*f* of the arm unit 5309, and communicably connecting these control boards to each other, functions similar to the microscope control device 5317 may be realized.

The endoscope device 5401 includes an endoscope 5403 for observation of the operating site 209 of the patient to be observed, an arm unit 5309 that supports the endoscope 5403 on the leading end, a base unit 5315 that supports the arm unit 5309 on the base end, and an endoscope control device 5417 that controls the operation of the endoscope device 5401. In the endoscope device 5401, the position and the attitude of the endoscope 5403 may be controlled arbitrarily by the arm unit 5309, within the movable range of the arm unit 5309. In other words, the endoscope device 5401 is configured to allow movement of the endoscope 5403 which includes the imaging function of the device, and thus may be considered to be a type of moving camera. In this way, by supporting the endoscope 5403 with the arm unit 5309, the positioning of the endoscope 5403 may be conducted with high precision, while in addition, the position and the attitude may be maintained in a desired state more reliably, thereby making it possible to obtain captured images more consistently.

The endoscope device 5401 corresponds to the microscope device 5301, but in which the arm unit 5309 supports the endoscope 5403 instead of the microscope unit 5303, and the microscope control device 5317 is replaced by the endoscope control device 5417. However, the functions of the endoscope control device 5417 are simply changed to perform image processing on an image signal acquired by the endoscope 5403, whereas other functions, such as the functions related to control of the operation of the arm unit 5309, for example, are similar to the microscope control device 5317. In this way, since the configuration of the arm unit 5309 and most of the functions of the endoscope control device 5417 are similar to the microscope device 5301, description will be reduced or omitted for the duplicate items herein.

The endoscope 5403 is made up of a lens tube 5405 having a region of certain length from the leading end that is inserted into a body cavity of a patient, and a camera head 5407 connected to the base end of the lens barrel 5405. In the example illustrated in the diagram, an endoscope 5403 configured as a so-called rigid scope having a rigid lens barrel 5405 is illustrated, but the endoscope 5403 may also be configured as a so-called flexible scope having a flexible lens barrel 5405.

On the leading end of the lens tube 5405, there is provided an opening into which an objective lens is fitted. A light source device (not illustrated) is connected to the endoscope 5403. Light generated by the light source device is guided up to the leading end of the lens tube by a light guide extending inside the lens tube 5405, and is radiated through the objective lens towards the operating site 209 to be observed inside the body cavity of the patient. Note that the endoscope 5403 may be a forward-viewing scope, an oblique-viewing scope, or a side-viewing scope.

An imaging unit made up of an optical system and an image sensor is provided inside the camera head 5407, and reflected light from the observation target (observation light) is guided inside the lens tube 5405, and then condensed onto the image sensor by the optical system. Observation light is photoelectrically converted by the image sensor, and an electrical signal corresponding to the observation light, or in other words, an image signal corresponding to the observed image, is generated. The image signal is transmitted to the endoscope control device 5417 as RAW data.

Note that the image unit may also include a driving mechanism that moves the zoom lens and the focus lens of the optical system along the optical axis. By suitably moving the zoom lens and the focus lens with the driving mechanism, the magnification factor of the captured image and the focus distance during imaging may be adjusted. By suitably driving the optical system, the imaging unit is provided with a function of adjusting the focus distance automatically (in other words, an AF function). Also, the imaging unit may be provided with any of various types of functions typically provided in endoscopes, such as an AE function.

In addition, to support stereoscopic vision (3D display) or the like, for example, the camera head 5407 may also be provided with multiple image sensors. In this case, multiple relay optical subsystems are provided to guide the observation light to each of the multiple image sensors.

The endoscope control device 5417 controls the operation of the endoscope device 5401. Specifically, the endoscope control device 5417 controls the driving of the arm unit 5309 in accordance with a certain control method, similarly to the microscope device 5301. Additionally, the endoscope control device 5417 changes the operating mode of the arm unit 5309. Also, the endoscope control device 5417 performs various types of signal processing on an image signal acquired by the imaging unit of the camera head 5407 of the endoscope 5403, and thereby generates image data for display. In other words, the endoscope control device 5417 includes the function of a CCU. For the signal processing, any of various known types of signal processing may be conducted, similarly to the microscope control device 5317.

The endoscope control device 5417 transmits information (endoscope image information) about the generated image data for display, or in other words a medical image taken by the endoscope 5403 (hereinafter also called an endoscope image), to the control device 109 at a certain interval corresponding to the frame rate of the medical image, for example. Also, at this point, the endoscope control device 5417 associates endoscope device status information indicating the status of the endoscope device 5401 (more specifically, the status of the endoscope 5403) with the endoscope image information as metadata, and transmits the metadata together with the endoscope image information to the control device 109. In the third embodiment, the endoscope device status information at least includes information about the current position and attitude of the endoscope 5403 obtained to control the arm unit 5309, and information about the focus distance of the endoscope 5403 adjusted by the AF function.

Note that the endoscope control device 5417 may be a processor such as a CPU or GPU, a control board on which a processor and a storage element such as memory are mounted, or the like. As a result of the processor of the endoscope control device 5417 operating in accordance with a certain program, the various functions described above may be realized. The specific device configuration of the endoscope control device 5417 may be similar to the microscope control device 5317.

Similarly to the first embodiment, the control device 109 includes an image decision unit 111 as a function. The image decision unit 111 decides a medical image to display on the display device 105 and a medical image to save in the storage device 107 (in other words, the medical image to adopt) from among the medical images respectively taken by the microscope device 5301 and the endoscope device 5401.

The image decision unit 111 decides which medical image to adopt on the basis of the microscope device status information and the endoscope device status information transmitted from the microscope device 5301 and the endoscope device 5401, respectively. At this point, in the third embodiment, similarly to the first embodiment, the image decision unit 111 decides a medical image including the operating site 209 to be observed from among the microscope image by the microscope device 5301 and the endoscope image from the endoscope device 5401 as the medical image to adopt.

Specifically, in the system 3, with regard to the status of the microscope device 5301 and the endoscope device 5401, a condition by which the operating site 209 is included in a captured image is respectively set in advance as an image decision condition. The image decision unit 111 determines whether or not the image decision condition is satisfied on the basis of the microscope device status information and the endoscope device status information, with regard to the status of the microscope device 5301 and the endoscope device 5401, respectively. Subsequently, from among the microscope image and the endoscope image, the image decision unit 111 decides, as the medical image to adopt, the medical image corresponding to the one for which the status of the microscope device 5301 and the status of the endoscope device 5401 satisfies the image decision condition.

For example, the image decision condition for the status of the microscope device 5301 is that the focus point of the microscope unit 5303 of the microscope device 5301 is aligned with the operating site 209. The position of the operating site 209 of the patient inside the operating room is already known. Since information about the position and the attitude of the microscope unit 5303 is transmitted as microscope status information from the microscope control device 5317 to the control device 109, the image decision unit 111 is able to use such information as a basis for computing the positional relationship between the microscope unit 5303 and the operating site 209. Also, information about the focus distance of the microscope unit 5303 is transmitted as microscope status information from the microscope control device 5317 to the control device 109. Consequently, the image decision unit 111 is able to determine whether or not the focus point of the microscope unit 5303 is aligned with the operating site 209 from the position of the operating site 209 inside the operating room, the computed positional relationship, and the information about the focus distance. In other words, the image decision unit 111 is able to determined whether or not the status of the microscope device 5301 satisfies the above image decision condition.

The above applies similarly to the endoscope device 5401. Since the position of the operating site 209 of the patient inside the operating room is already known, and information about the position and the attitude of the endoscope 5403 is transmitted as endoscope status information from the endoscope control device 5417 to the control device 109, the image decision unit 111 is able to use such information as a basis for computing the positional relationship between the endoscope 5403 and the operating site 209. Also, information about the focus distance of the endoscope 5403 is transmitted as endoscope status information from the endoscope control device 5417 to the control device 109. Consequently, the image decision unit 111 is able to determine whether or not the focus point of the endoscope 5403 is aligned with the operating site 209 from the position of the operating site 209 inside the operating room, the computed positional relationship, and the information about the focus distance. In other words, the image decision unit 111 is able to determined whether or not the status of the endoscope device 5401 satisfies the above image decision condition.

If the determination result indicates that at least one of the status of the microscope device 5301 and the status of the endoscope device 5401 satisfies the above image decision condition, the image decision unit 111 decides, as the medical image to adopt, the medical image taken by the device satisfying the image decision condition from among the microscope device 5301 and the endoscope device 5401.

Herein, in the first and second embodiments, from among the medical images respectively taken by multiple imaging devices (the field of view camera 101 and the operating field camera 103 in the first embodiment, or the multiple moving cameras 121 in the second embodiment), one medical image is decided as the medical image to adopt. However, in the third embodiment, if the image decision condition is satisfied, multiple medical images may be adopted. In other words, in the third embodiment, if the status of the microscope device 5301 satisfies the image decision condition but the status of the endoscope device 5401 does not satisfy the image decision condition, the image decision unit 111 decides the microscope image as the medical image to adopt. Meanwhile, if the status of the microscope device 5301 does not satisfy the image decision condition but the status of the endoscope device 5401 satisfies the image decision condition, the image decision unit 111 decides the endoscope image as the medical image to adopt. Meanwhile, if the status of the microscope device 5301 and the status of the endoscope device 5401 both satisfy the image decision condition, the image decision unit 111 decides both the microscope image and the endoscope image as the medical images to adopt.

Note that if neither the image decision condition for the status of the microscope device 5301 nor the image decision condition for the status of the endoscope device 5401 is satisfied, the image decision unit 111 may also adopt neither the field of view image nor the operating field image. This is because in this case, it is conceivable that the operating site 209 is not depicted clearly in either microscope image or the endoscope image, and thus there is little or no significance in displaying and saving such medical images.

After deciding the medical image to adopt, the image decision unit 111 controls the operation of the display device 105 to display the decided medical image on the display device 105. Additionally, the image decision unit 111 controls the operation of the storage device 107 to save the decided medical image in the storage device 107. At this point, the image decision unit 111 also saves metadata associated with the decided medical image (that is, microscope device status information if the decided medical image is the microscope image, or endoscope device status information if the decided medical image is the endoscope image) together with the medical image.

If both medical images are adopted, both the microscope image and the endoscope image are displayed on the display device 105. For example, the display screen of the display device 105 may be split into two regions, and the microscope image and the endoscope image may be displayed respectively in the two regions. Alternatively, multiple display devices 105 may be provided, and the microscope image and the endoscope image may be displayed respectively on each of the display devices 105.

At this point, in a surgery that uses both the microscope device 5301 and the endoscope device 5401 like in the system 3, a conceivable way of performing the surgery is to observe the surface of the operating site 209 with the microscope image, while also observing the interior or the underside of the operating site 209 with the endoscope image, for example. In this way, since the usage and purpose of the microscope image and the endoscope image are different, there is significance in displaying and saving both images. However, there is no point in displaying and saving medical images that do not include the operating site 209, or medical images in which the operating site 209 is unclear. Consequently, in the third embodiment, if only one device satisfies the image decision condition, the medical image corresponding to the device that satisfies the image decision condition is displayed and saved, whereas if both devices satisfy the image decision condition, both medical images are displayed and saved. Thus, more appropriate management of medical images becomes possible.

The above thus describes a configuration of the system 3 according to the third embodiment. Note that in the above description, the microscope device status information includes information about the current position and attitude of the microscope unit 5303 as well as the focus distance of the microscope unit 5303, while the endoscope device status information includes information about the current position and attitude of the endoscope 5403 as well as the focus distance of the endoscope 5403, but the third embodiment is not limited to such an example. It is sufficient for the microscope device status information and the endoscope device status information to include information that may contribute to the determination of the image decision condition stipulating that the focus point is aligned with the operating site 209, and thus the above information may not necessarily be included, and any of various other types of information may also be included.

3-2. Control Method

A processing sequence of a control method in the system 3 according to the third embodiment described above will be described with reference to FIG. 10. FIG. 10 is a flowchart illustrating an example of a processing sequence of a control method according to the third embodiment. Note that each process illustrated in FIG. 10 corresponds to a process executed by the control device 109 illustrated in FIGS. 8 and 9. As a result of the processor constituting the control device 109 operating in accordance with a certain program, the respective processes illustrated in FIG. 10 are executed. Since the details of each process illustrated in FIG. 10 have already been described earlier in the description of the functions of the control device 109, in the following description of the processing sequence of the control method according to the third embodiment, an overview of each process will be described briefly, and detailed description will be reduced or omitted.

Referring to FIG. 10, in the control method according to the third embodiment, first, microscope image information and microscope device status information is acquired from the microscope device 5301 (step S301). The process in step S301 corresponds to the process in which microscope image information and microscope device status information is transmitted from the microscope device 5301 illustrated in FIGS. 8 and 9 to the control device 109.

Next, endoscope image information and endoscope device status information is acquired from the endoscope device 5401 (step S303). The process in step S303 corresponds to the process in which endoscope image information and endoscope device status information is transmitted from the endoscope device 5401 illustrated in FIGS. 8 and 9 to the control device 109. Note that in FIG. 10, the process in step S301 and the process in step S303 are described as being conducted sequentially for the sake of convenience, but during actual surgery, the process in step S301 and the process in step S303 may be executed in parallel on a certain interval for each (for example, a certain interval corresponding to the respective frame rate of the microscope image and the endoscope image).

Next, on the basis of the microscope device status information and the endoscope device status information, the medical image to adopt is decided from among the microscope image and the endoscope image (step S305). The process in step S305 corresponds to the process executed by the image decision unit 111 of the control device 109 illustrated in FIGS. 8 and 9. At this point, in the third embodiment, either one of the microscope image or the endoscope image may be adopted in some cases, or both the microscope image and the endoscope image may be adopted in some cases.

Subsequently, the decided medical image is displayed on the display device 105 while also being saved to the storage device 107 (step S307). The process in step S307 corresponds to the process executed by the image decision unit 111 of the control device 109 illustrated in FIGS. 8 and 9 to respectively control the operation of the display device 105 and the storage device 107.

The above thus describes a processing sequence of a control method according to the third embodiment.

4. Fourth Embodiment 4-1. Configuration of System

A configuration of a system according to a fourth embodiment will be described with reference to FIGS. 11 and 12. FIG. 11 is a diagram illustrating a diagrammatic configuration of a system according to the fourth embodiment. FIG. 12 is a block diagram illustrating a functional configuration of a system according to the fourth embodiment. FIG. 11 illustrates a situation in which surgery is being performed on a patient 203 lying on an operating table 205, and the state of the surgery is being captured using a system 4 according to the fourth embodiment.

Referring to FIGS. 11 and 12, the system 4 according to the fourth embodiment is provided with an X-ray image-taking device 131 that takes X-ray tomographic images of the patient 203 during surgery, an ultrasound image-taking device 133 that takes an ultrasound image inside the blood vessels of the patient 203, a display device 105 which is installed inside the operating room and which displays the intravascular image taken by the ultrasound image-taking device 133 while also displaying at least one of the multiple X-ray tomographic images taken by the X-ray image-taking device 131 and depicting different locations in the body of the patient 203, a storage device 107 that saves image information corresponding to a medical image displayed on the display device 105, and a control device 109 that decides which X-ray tomographic image to display on the display device 105 and which X-ray tomographic image to save in the storage device 107. In this way, the system 4 corresponds to the system 1 according to the first embodiment described above being provided with the X-ray image-taking device 131 and the ultrasound image-taking device 133 instead of the field of view camera 101 and the operating field camera 103. In other words, the system 4 is applied favorably to surgery that uses the X-ray image-taking device 131 and the ultrasound image-taking device 133 jointly.

The X-ray image-taking device 131 is provided with a C-arm, and takes X-ray tomographic images of the patient 203 while the C-arm moves in lengthwise direction of the operating table 205 (in other words, the height direction of the patient 203). In this way, the X-ray image-taking device 131 is a device that takes images while moving a C-arm that includes the imaging function, and thus may be considered to be a type of moving camera. For the sake of simplicity, FIG. 11 illustrates only the C-arm as the X-ray image-taking device 131, but the X-ray image-taking device 131 may have a configuration similar to a typical X-ray image-taking device including a C-arm. Since the specific configuration of the X-ray image-taking device 131 may be similar to a typical X-ray image-taking device including a C-arm, detailed description will be reduced or omitted herein.

The X-ray image-taking device 131 transmits information about a taken X-ray tomographic image (X-ray tomographic image information) to the control device 109 at a certain interval corresponding to the frame rate of the X-ray tomographic image, for example. In other words, multiple X-ray tomographic images depicting different locations in the body of the patient 203 are taken by the X-ray image-taking device 131, and information about such multiple X-ray tomographic images is transmitted to the control device 109. Also, at this point, the X-ray image-taking device 131 associates X-ray image-taking device status information indicating the status of the X-ray image-taking device 131 with the X-ray tomographic image information as metadata, and transmits the metadata together with the X-ray tomographic image information to the control device 109. In the fourth embodiment, the X-ray image-taking device status information at least includes information about the position of the C-arm with respect to the patient 203.

The ultrasound image-taking device 133 includes a catheter 135 with an ultrasound transmitting/receiving device mounted on the leading end. By transmitting and receiving ultrasound with the ultrasound transmitting/receiving device while also moving the catheter 135 inside the blood vessels of the patient 203, the ultrasound image-taking device 133 takes ultrasound images inside the blood vessels of the patient 203. The ultrasound image-taking device 133 is a device for obtaining what are called intravascular ultrasound (IVUS) images. With the ultrasound image-taking device 133, ultrasound images of a cross-section of blood vessels may be obtained. For the sake of simplicity, FIG. 11 illustrates a simplified view of the ultrasound image-taking device 133, but the ultrasound image-taking device 133 may have a configuration similar to a typical ultrasound image-taking device capable of taking IVUS images. Since the specific configuration of the ultrasound image-taking device 133 may be similar to a typical ultrasound image-taking device capable of taking IVUS images, detailed description will be reduced or omitted herein.

The ultrasound image-taking device 133 transmits information about a taken ultrasound image (ultrasound image information) to the control device 109 at a certain interval corresponding to the frame rate of the ultrasound image, for example. In other words, multiple ultrasound images depicting different locations inside the blood vessels of the patient 203 are taken by the ultrasound image-taking device 133, and information about such multiple ultrasound images is transmitted to the control device 109. Also, at this point, the ultrasound image-taking device 133 associates ultrasound image-taking device status information indicating the status of the ultrasound image-taking device 133 with the ultrasound image information as metadata, and transmits the metadata together with the ultrasound image information to the control device 109. In the fourth embodiment, the ultrasound image-taking device status information at least includes information about the position of the leading end of the catheter 135 inside the blood vessels of the patient 203. Such a position of the leading end of the catheter 135 may be realized by attaching a marker to the leading end of the catheter 135, and detecting the marker from outside the body with any of various known types of position sensors or the like, for example.

Similarly to the first embodiment, the control device 109 includes an image decision unit 111 as a function. The image decision unit 111 decides a medical image to display on the display device 105 and a medical image to save in the storage device 107 (in other words, the medical image to adopt), on the basis of the X-ray image-taking device status information transmitted from the X-ray image-taking device 131 and the ultrasound image-taking device status information transmitted from the ultrasound image-taking device 133.

At this point, in the first to third embodiments described earlier, the image decision unit 111 decides the medical image to adopt from among medical images respectively taken by multiple imaging devices. However, in the fourth embodiment, the image decision unit 111 constantly decides to adopt the most recent ultrasound image taken by the ultrasound image-taking device 133. Additionally, regarding the X-ray tomographic images taken by the X-ray image-taking device 131, the image decision unit 111 decides, as the medical image to adopt, one of the multiple X-ray tomographic images depicting different locations in the body of the patient 203, on the basis of the X-ray image-taking device status information and the ultrasound image-taking device status information. At this point, from among the multiple X-ray tomographic images, the image decision unit 111 decides, as the medical image to adopt, the X-ray tomographic image corresponding to the position of the blood vessel appearing in the ultrasound image taken by the ultrasound image-taking device 133.

Specifically, in the system 4, with regard to the status of the X-ray image-taking device 131, an image decision condition is set in advance. The image decision unit 111 determines whether or not the image decision condition is satisfied on the basis of the X-ray image-taking device status information and the ultrasound image-taking device status information. Subsequently, from among the multiple X-ray tomographic images, the image decision unit 111 decides, as the medical image to adopt, the X-ray tomographic image corresponding to the one for which the image decision condition is satisfied.

In the system 4, the image decision condition is that the X-ray tomographic image includes the site to be observed which is captured in the ultrasound image taken by the ultrasound image-taking device 133. As described above, in the ultrasound image-taking device 133, an ultrasound image inside the blood vessels is obtained by the ultrasound transmitting/receiving device provided on the leading end of the catheter 135. In other words, the site which is captured in an ultrasound image taken by the ultrasound image-taking device 133 is the site where the leading end of the catheter 135 is positioned. Meanwhile, in the X-ray image-taking device 131, X-ray tomographic images are obtained by the C-arm. In other words, the site which is captured in an X-ray tomographic image taken by the X-ray image-taking device 131 is the site where the C-arm is positioned. In other words, if the position of the C-arm corresponds to the position of the leading end of the catheter 135, the above image decision condition may be treated as being satisfied. Consequently, the image decision unit 111 is able to determine whether or not the status of the X-ray image-taking device 131 satisfies the above image decision condition, on the basis of the position information about the C-arm included in the X-ray image-taking device status information, and the position information about the leading end of the catheter 135 included in the ultrasound image-taking device status information. Subsequently, on the basis of the determination result, the image decision unit 111 is able to decide, as the medical image to adopt, the X-ray tomographic image capturing the tomographic slice that includes the site which is captured in the ultrasound image taken by the ultrasound image-taking device 133 from among the multiple X-ray tomographic images corresponding to different sites in the body of the patient 203 taken by the X-ray image-taking device 131.

After deciding which X-ray image to adopt, the image decision unit 111 controls the operation of the display device 105 to display the decided ultrasound image and the decided X-ray tomographic image corresponding to the ultrasound image on the display device 105. Additionally, the image decision unit 111 controls the operation of the storage device 107 to save the decided ultrasound image and the decided X-ray tomographic image corresponding to the ultrasound image in the storage device 107. At this point, the image decision unit 111 also saves the metadata associated with the decided medical images (namely, the X-ray image-taking device status information associated with the decided X-ray tomographic image and the ultrasound image-taking device status information associated with the decided ultrasound image) together with the medical images.

FIG. 13 is a diagram illustrating an exemplary display on the display device 105 in the system 4 according to the fourth embodiment. As illustrated in FIG. 13, in the fourth embodiment, an X-ray tomographic image 213 and an ultrasound image 215 are both displayed on a display screen 211 of the display device 105. According to the decision process conducted by the image decision unit 111 described above, images depicting the same corresponding site in the body of the patient 203 are displayed as the X-ray tomographic image 213 and the ultrasound image 215. At this point, as illustrated in the diagram, the image decision unit 111 may also overlay onto the X-ray tomographic image 213 an icon 217 indicating the site corresponding to the ultrasound image 215. Consequently, the surgeon 201 becomes able to intuitively grasp the site captured by the ultrasound image. In the decision process described above, the image decision unit 111 specifies the site captured by the X-ray tomographic image and the site captured by the ultrasound image on the basis of the X-ray image-taking device status information and the ultrasound image-taking device status information, and thus the icon 217 may be displayed on the basis of the results of such a decision process.

At this point, in the ultrasound image-taking device 133 for obtaining what are called IVUS images, the technology for accurately ascertaining the position of the leading end of the catheter 135 is not adequately established, and there is demand to ascertain more accurately which blood vessel site is being depicted by the taken ultrasound image. To meet such demand, in the fourth embodiment as described above, the X-ray image-taking device 131 is combined with the ultrasound image-taking device 133, and in addition, the ultrasound image and the X-ray tomographic image obtained by these devices are associated together and the site of the body captured by the ultrasound image may be indicated on the X-ray tomographic image. Consequently, such demand may be met, and smoother execution of surgery may be realized.

The above thus describes a configuration of the system 4 according to the fourth embodiment. Note that in the above description, the X-ray image-taking device status information includes information about the position of the C-arm with respect to the patient 203, and the ultrasound image-taking device status information includes information about the position of the leading end of the catheter 135 inside the blood vessels of the patient 203, but the fourth embodiment is not limited to such an example. It is sufficient for the X-ray image-taking device status information and the ultrasound image-taking device status information to include information that may be contribute to the determination of the image decision condition stipulating that the X-ray tomographic image depicts the site depicted by the ultrasound image taken by the ultrasound image-taking device 133, and thus the above information may not necessarily be included, and any of various other types of information may also be included.

4-2. Control Method

A processing sequence of a control method in the system 4 according to the fourth embodiment described above will be described with reference to FIG. 14. FIG. 14 is a flowchart illustrating an example of a processing sequence of a control method according to the fourth embodiment. Note that each process illustrated in FIG. 14 corresponds to a process executed by the control device 109 illustrated in FIGS. 11 and 12. As a result of the processor constituting the control device 109 operating in accordance with a certain program, the respective processes illustrated in FIG. 14 are executed. Since the details of each process illustrated in FIG. 14 have already been described earlier in the description of the functions of the control device 109, in the following description of the processing sequence of the control method according to the fourth embodiment, an overview of each process will be described briefly, and detailed description will be reduced or omitted.

Referring to FIG. 14, in the control method according to the fourth embodiment, first, X-ray tomographic image information and X-ray image-taking device status information is acquired from the X-ray image-taking device 131 (step S401). The process in step S401 corresponds to the process in which X-ray tomographic image information and X-ray image-taking device status information is transmitted from the X-ray image-taking device 131 illustrated in FIGS. 11 and 12 to the control device 109.

Next, ultrasound image information and ultrasound image-taking device status information is acquired from the ultrasound image-taking device 133 (step S403). The process in step S403 corresponds to the process in which ultrasound image information and ultrasound image-taking device status information is transmitted from the ultrasound image-taking device 133 illustrated in FIGS. 11 and 12 to the control device 109. Note that in FIG. 14, the process in step S401 and the process in step S403 are described as being conducted sequentially for the sake of convenience, but during actual surgery, the process in step S401 and the process in step S403 may be executed in parallel on a certain interval for each (for example, a certain interval corresponding to the respective frame rate of the X-ray tomographic image and the ultrasound image).

Next, the ultrasound image is decided as the medical image to adopt (step S405). Subsequently, on the basis of the X-ray image-taking device status information and the ultrasound image-taking device status information, the medical image to adopt is decided from among multiple X-ray tomographic images depicting different sites in the body of the patient 203 (step S407). The process in step S405 and the process in step S407 correspond to the process executed by the image decision unit 111 of the control device 109 illustrated in FIGS. 11 and 12. In this way, in the fourth embodiment, for the ultrasound image, the most recent image is constantly decided as the medical image to adopt, whereas for the X-ray tomographic image, one X-ray tomographic image from among multiple X-ray tomographic images is decided as the medical image to adopt.

Subsequently, the decided medical image is displayed on the display device 105 while also being saved to the storage device 107 (step S409). The process in step S409 corresponds to the process executed by the image decision unit 111 of the control device 109 illustrated in FIGS. 11 and 12 to respectively control the operation of the display device 105 and the storage device 107.

The above thus describes a processing sequence of a control method according to the fourth embodiment.

5. Conclusion and Supplementary Remarks

As described above, according to the second to the fourth embodiments, similarly to the first embodiment, the medical image to adopt is decided without using image analysis results, thereby making it possible to manage medical images more appropriately. Consequently, the work of editing medical images becomes unnecessary, and in addition, a reduction in the amount of data saved in the storage device 107 may be realized. Also, in the second to fourth embodiments, it becomes possible to appropriately manage medical images taken by multiple moving cameras, on the basis of position information and/or attitude information about the multiple moving cameras. As described earlier when describing the first embodiment, since a medical image from a moving camera may be a significant as a medical image indicating the state of surgery, according to the second to fourth embodiments, a merit of becoming able to manage such significant medical images more appropriately may be conferred.

Note that the respective items described in the first to fourth embodiments above may also be combined with each other where possible. For example, any of the various imaging devices described above may be combined arbitrarily to configure a system. For example, a system may be configured to be provided with multiple moving cameras (including field of view cameras) and an operating field camera. In this case, on the basis of imaging device status information about the imaging devices, the medical image to adopt may be decided from among the medical images taken by these imaging devices so that a suitably set image decision condition is satisfied. Additionally, the first to fourth embodiments may also be configured as follows.

For example, in the systems 1 to 4 described above, taken medical images are displayed and saved, but the first to fourth embodiments are not limited to such an example. The systems 1 to 4 may also be provided with only one of the display device 105 and the storage device 107, and the image decision unit 111 may decide only one of a medical image to display on the display device 105 and a medical image to save in the storage device 107. Whether the display device 105 or the storage device 107 is to be provided may be decided suitably in accordance with the purpose of managing the medical images. For example, if the primary purpose is to share information during surgery, the systems 1 to 4 may be provided with the display device 105 only. On the other hand, if the primary purpose is to record the state of surgery for the purpose of education, training, and the like, the systems 1 to 4 may be provided with the storage device 107 only.

In addition, in the systems 1 to 4 described above, the results of analyzing captured images are not used when deciding the medical image to adopt, but the first to fourth embodiments are not limited to such an example. In the control device 109 of the systems 1 to 4, image analysis may be conducted on medical images taken by multiple imaging devices, and a process of deciding the medical image to adopt that takes the image analysis results into account may be conducted. Image analysis results contain much useful information, and thus by taking the image analysis results into account, it becomes possible to adopt more suitable medical images. For example, in the first to third embodiments, image analysis results may be used to determine whether or not the affected area to be observed is included in a captured image. Alternatively, imaging device status information may be acquired on the basis of image analysis results. For example, in the fourth embodiment, the position of the marker on the leading end of the catheter 135 of the ultrasound image-taking device 133 may be specified on the basis of a result of analyzing an X-ray tomographic image taken by the X-ray image-taking device 131, and thus position information about the leading end of the catheter 135 may be acquired as ultrasound image-taking device status information. In this case, position information about the leading end of the catheter 135 is transmitted as ultrasound image-taking device status information from the X-ray image-taking device 131 to the control device 109. However, as described earlier, image analysis often involves large amounts of calculation time, and if image analysis results are used, there is a risk of becoming unable to conduct the process of deciding which medical image to adopt rapidly. Consequently, in the first to fourth embodiments, image analysis results preferably are used only in an auxiliary manner, such as jointly using image analysis results only in special circumstances in which the desired accuracy is difficult to obtain in a determination process based on captured image status information, for example.

In addition, the systems 1 to 4 described above deal with medical images taken during surgery, but the first to fourth embodiments are not limited to such an example. The systems 1 to 4 may also manage medical images taken in the middle of other medical procedures, such as examinations, for example. In this way, the target to which the systems 1 to 4 are applied may be any type of medical procedure.

Herein, as described above, the purpose of taking medical images in the first to fourth embodiments is to share the state of a operating site during surgery with other medical staff, to leave a record of the surgery, to create educational materials for young doctors, and so on. On the other hand, another purpose may be to use the medical images that have been taken and saved as a data set for constructing an artificial intelligence (AI) for an autonomous surgical assistance robotic device. For example, medical images indicating the field of view of the surgeon during surgery may be useful information when constructing a motion algorithm for such a surgical assistance robotic device. Herein, in the first to fourth embodiments, as described earlier, when image information is saved in the storage device 107, metadata is also saved at the same time. Such metadata may be information that indicates the state of the movement of an field of view camera, or in other words, information that indicates the state of the movement of the surgeon's field of view during surgery, for example, and thus such metadata may also be useful information when constructing a motion algorithm for a surgical assistance robotic device. By applying the systems 1 to 4 according to the first to fourth embodiments, suitable image information that includes the state of the operating site is saved as needed more consistently and automatically, and thus a huge amount of appropriate image information may be accumulated by repeated surgeries. In this way, by applying the systems 1 to 4, it becomes possible to more efficiently obtain data that is useful for the development of an AI for a surgical assistance robotic device.

It should be understood by those skilled in the art that various modifications, combinations, sub-combinations and alterations may occur depending on design requirements and other factors insofar as they are within the scope of the appended claims or the equivalents thereof.

For example, the target of application of the technology according to the present disclosure is not limited to the medical field, and may also be fields other than the medical field. When capturing a certain observation target with multiple image-taking devices, if there is a situation that demands appropriate management of captured images taken respectively by the multiple image-taking devices (that is, selecting images that depict the observation target more reliably), the technology according to the present disclosure may be applied to thereby enable such captured images to be managed more appropriately.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

A control device that decides at least one medical image as a medical image to display or save from among medical images taken by a plurality of imaging devices, on a basis of imaging device status information that includes information about a position or an attitude for at least one of the plurality of imaging devices.

(2)

The control device according to (1), in which the plurality of imaging devices includes at least one moving camera.

(3)

The control device according to (2), in which the moving camera is a field of view camera worn by a medical staff member.

(4)

The control device according to (2) or (3), in which the moving camera is attached to a treatment tool used in a medical procedure.

(5)

The control device according to any one of (2) to (4), in which the moving camera is a microscope device that takes an image of an observation target with a microscope unit attached to a leading end of an arm unit.

(6)

The control device according to any one of (2) to (5), in which the moving camera is an endoscope device that takes an image of an observation target with an endoscope attached to a leading end of an arm unit.

(7)

The control device according to any one of (2) to (6), in which the moving camera is an X-ray image-taking device that takes an X-ray tomographic image of a patient while moving an imaging unit relative to the patient.

(8)

The control device according to any one of (2) to (7), in which the moving camera is an ultrasound image-taking device that takes an ultrasound image inside a blood vessel of a patient while moving a catheter provided with an imaging unit on a leading end inside the blood vessel.

(9)

The control device according to any one of (1) to (8), in which the control device determines whether or not a status of at least one of the plurality of imaging devices satisfies a certain image decision condition on a basis of the imaging device status information, and decides a medical image taken by the imaging device that satisfies the image decision condition as the medical image to display or save, and the image decision condition is that an observation target is included in the medical image.

(10)

The control device according to (9), in which the plurality of imaging devices includes a field of view camera, which is a moving camera attached to a head of a medical staff member, and an operating field camera, which is installed in a stationary manner inside an operating room, the imaging device status information about the field of view camera includes information about an attitude of the field of view camera, the imaging device status information about the operating field camera includes information about a focus distance of the operating field camera, if the field of view camera is tilted by a certain angle or more, the control device determines that the status of the field of view camera satisfies the image decision condition, and if a focus point of the operating field camera is aligned with the observation target, the control device determines that the status of the operating field camera satisfies the image decision condition, and on a basis of a determination result, the control device decides one of a medical image taken by the field of view camera and a medical image taken by the operating field camera as the medical image to display or save.

(11)

The control device according to (9), in which the plurality of imaging devices includes a plurality of moving cameras, the imaging device status information about each of the plurality of moving cameras includes information about a position of the moving camera and information about a focus distance of the moving camera, if a focus point of one of the plurality of moving cameras is aligned with the observation target, the control device determines that the status of the moving camera satisfies the image decision condition, and on a basis of a determination result, the control device decides one from among medical images respectively taken by the plurality of moving cameras as the medical image to display or save.

(12)

The control device according to (9), in which the plurality of imaging devices includes a microscope device that takes an image of an observation target with a microscope unit attached to a leading end of an arm unit, and an endoscope device that takes an image of an observation target with an endoscope attached to a leading end of an arm unit, the imaging device status information about the microscope device includes information about a position and information about a focus distance of the microscope unit, the imaging device status information about the endoscope device includes information about a position and information about a focus distance of the endoscope, if a focus point of the microscope unit is aligned with the observation target, the control device determines that the status of the microscope device satisfies the image decision condition, and if a focus point of the endoscope is aligned with the observation target, the control device determines that the status of the endoscope device satisfies the image decision condition, and on a basis of a determination result, the control device decides one or both of a medical image taken by the microscope device and a medical image taken by the endoscope device as the medical image to display or save.

(13)

The control device according to (9), in which the plurality of imaging devices includes an X-ray image-taking device that takes an X-ray tomographic image of a patient while moving an imaging unit for taking X-ray images relative to the patient, and an ultrasound image-taking device that takes an ultrasound image inside a blood vessel of a patient while moving a catheter provided with an imaging unit for taking ultrasound images on a leading end inside the blood vessel, the imaging device status information about the X-ray image-taking device includes information about a position of the imaging unit for taking X-ray images, the imaging device status information about the ultrasound image-taking device includes information about a position of the imaging unit for taking ultrasound images, if the position of the imaging unit for taking X-ray images corresponds to the position of the imaging unit for taking ultrasound images, the control device determines that the status of the X-ray image-taking device satisfies the image decision condition, and the control device decides an ultrasound image of the inside of the blood vessel of the patient taken by the ultrasound image-taking device as the medical image to display or save, and in addition, on a basis of a determination result, decides, as the medical image to display or save, an X-ray tomographic image that includes a site being depicted by the ultrasound image from among a plurality of X-ray tomographic images depicting different sites in a body of the patient taken by the X-ray image-taking device.

(14)

The control device according to (13), in which when the control device causes a display device to display the ultrasound image and the X-ray tomographic image decided as the medical images to display, the control device overlays onto the X-ray tomographic image an icon indicating the site being depicted by the ultrasound image.

(15)

The control device according to any one of (1) to (14), in which the control device causes at least one medical image decided as the medical image to display or save to be displayed on a display unit or saved in a storage unit.

(16)

The control device according to any one of (1) to (15), in which the imaging device status information includes information about a position and an attitude of at least one of the plurality of imaging devices.

(17)

The control device according to any one of (1) to (16), in which the control device decides at least one medical image from among medical images taken by the plurality of imaging devices as a medical image to display and save.

(18)

A control method, including:

deciding at least one medical image as a medical image to display or save from among medical images taken by a plurality of imaging devices, on a basis of imaging device status information that includes information about a position or an attitude for at least one of the plurality of imaging devices.

(19)

A medical system, including:

a plurality of imaging devices; and a control device that decides at least one medical image as a medical image to display or save from among medical images taken by the plurality of imaging devices, on a basis of imaging device status information that includes information about a position or an attitude for at least one of the plurality of imaging devices.

(20)

A medical control device for a medical imaging system, comprising:

processing circuitry configured to select at least one medical image from among a plurality of medical images obtained by a plurality of medical imaging devices, the selection being based on medical imaging device status information that includes three dimensional information of at least one of the plurality of medical imaging devices, and output the selected at least one medical image from the plurality of medical images obtained by the plurality of medical imaging devices.

(21)

The medical control device according to (20), wherein the plurality of imaging devices includes at least one movable camera.

(22)

The medical control device according to (21), wherein the movable camera is a wearable camera.

(23)

The medical control device according to (22), wherein the movable camera is attached to a treatment tool used in a medical procedure.

(24)

The medical control device according to (21), wherein the movable camera is a microscope camera that obtains an image of an observation target with a microscope being attached to a leading end of an arm.

(25)

The medical control device according to (24), wherein the movable camera is an endoscope camera that obtains an image of an observation target with an endoscope being attached to a leading end of an arm.

(26)

The medical control device according to (21), wherein the movable camera is an X-ray camera that obtains an X-ray tomographic image while moving relative to a patient body.

(27)

The medical control device according to (21), wherein the movable camera is an ultrasound that obtains an ultrasound image inside a blood vessel while moving a catheter provided with a transducer on a leading end, inside the blood vessel.

(28)

The medical control device according to (20), wherein the processing circuitry is further configured to determine whether or not a status of at least one of the plurality of medical imaging devices satisfies a certain image decision condition based on the imaging device status information, and select the at one medical image from among a plurality of medical images obtained by a medical imaging device that satisfies the image decision condition, and wherein the image decision condition is that an observation target is included in the medical image.

(29)

The medical control device according to (28), wherein the plurality of imaging devices includes a movable camera which is a point of view camera, and surgical field camera, which is installed in a stationary manner inside an operating room, the imaging device status information about the point of view camera includes information about the three-dimensional posture of the camera, the imaging device status information about the surgical field camera includes information about a distance between the surgical field camera and a focus point of the surgical field camera, and wherein the processing circuitry is further configured to determine, when the point of view camera is tilted by a certain angle or more, that the status of the point of view camera satisfies the image decision condition, determine, when the focus point of the surgical field camera is aligned with the observation target, that the status of the surgical field camera satisfies the image decision condition, and select the at least one medical image from among a plurality of medical images obtained by the point of view camera and from among a plurality of medical images obtained by the surgical field camera based on the respective status of the point of view camera and the surgical field camera satisfying the image decision condition.

(30)

The medical control device according to (28), wherein the plurality of imaging devices includes a plurality of movable cameras, the imaging device status information about each of the plurality of movable cameras includes information about a position of the respective movable camera and information about a distance between the respective movable camera and a respective focus point of the movable camera, wherein when the respective focus point of the respective movable camera is aligned with the observation target, the control device determines that the status of the respective moving camera satisfies the image decision condition, and selects the at least one medical image from among a plurality of medical images obtained by the plurality of movable cameras based on the statuses of the plurality of movable cameras satisfying the image decision condition.

(31)

The medical control device according to (28), wherein the plurality of imaging devices includes a microscope camera that obtains an image of an observation target with a microscope attached to a leading end of an arm, and an endoscope camera that obtains an image of an observation target with an endoscope attached to a leading end of an arm, the imaging device status information about the microscope camera includes information about a position and information about a distance between the microscope camera and a focus point of the microscope camera, the imaging device status information about the endoscope camera includes information about a position and information about a distance between the endoscope camera and a focus point of the endoscope camera, and wherein the processing circuitry is further configured to determine, when the focus point of the microscope camera is aligned with the observation target, that the status of the microscope camera satisfies the image decision condition, and determine, when a focus point of the endoscope camera is aligned with the observation target, that the status of the endoscope camera satisfies the image decision condition, and select the at least one medical image from among a plurality of medical images obtained by the microscope and from among a plurality of medical images obtained by the endoscope camera based on the respective status of the microscope camera and the endoscope camera satisfying the image decision condition.

(32)

The medical image filtering device according to (28), wherein the plurality of imaging devices includes an X-ray camera that obtains an X-ray tomographic image while moving relative to a patient body, and an ultrasound that obtains an ultrasound image inside a blood vessel while moving a catheter provided with a transducer for obtaining ultrasound images on a leading end inside the blood vessel, the imaging device status information about the X-ray camera includes information about a position of the X-ray camera, the imaging device status information about the ultrasound includes information about a position of the transducer, and wherein the processing circuitry is further configured to determine, when the position of the X-ray camera corresponds to the position of the ultrasound, that the status of the X-ray camera satisfies the image decision condition, and select the at least one medical image from among an ultrasound image of the inside of the blood vessel obtained by the ultrasound and an X-ray tomographic image that includes a site being depicted by the ultrasound image from among a plurality of X-ray tomographic images depicting different sites in a body.

(33)

The medical control device according to (32), wherein when the at least one medical image displayed on a display device includes the ultrasound image and the X-ray tomographic image, the processing circuitry is further configured to overlay onto the X-ray tomographic image an icon indicating the site being depicted by the ultrasound image.

(34)

The medical control device according to (20), wherein the processing circuitry is further configured to select at least two medical images from among the plurality of medical images obtained by a plurality of medical imaging devices.

(35)

The medical control device according to (20), wherein the three dimensional information of the imaging device status information further includes information about at least one of a three dimensional location and a three dimensional posture of at least one of the plurality of medical imaging devices.

(36)

The medical control device according to (20), wherein the processing circuitry is further configured to discard any medical images of the plurality of medical images obtained by the plurality of medical imaging devices that are not selected.

(37)

The medical control device according to (20), wherein the processing circuitry is further configured to filter any remaining medical images of the plurality of medical images that are not selected by the processing circuitry by selectively displaying or recording only the selected at least one medical image.

(38)

The medical control device according to (20), wherein the medical imaging device status information includes occlusion information and images of the plurality of medical images having the occlusion information indicating surgical field occlusion are not selected.

(39)

A medical control method, comprising:
selecting at least one medical image from among a plurality of medical images obtained by a plurality of medical imaging devices, the selecting being based on medical imaging device status information that includes three dimensional information of at least one of the plurality of medical imaging devices; and
outputting the selected at least one medical image from the plurality of medical images obtained by the plurality of medical imaging devices.

(40)

A medical imaging and control system, comprising:
a plurality of medical imaging devices; and
processing circuitry configured to
select at least one medical image from among a plurality of medical images obtained by the plurality of medical imaging devices, the selection being based on medical imaging device status information that includes information about a three-dimensional posture of at least one of the plurality of medical imaging devices, and
output the selected at least one medical image from the plurality of medical images obtained by the plurality of medical imaging devices.

REFERENCE SIGNS LIST 1, 2, 3, 4 system
101 field of view camera (point of view camera, head mount camera)
103 operating field camera
105 display device
107 storage device
109 control device
111 image decision unit
121 moving camera
123 position sensor
131 X-ray image-taking device
133 ultrasound image-taking device
5301 microscope device
5401 endoscope device

The invention claimed is:

1. A medical control device for a medical imaging system, comprising:
processing circuitry configured to
determine a status of each of a plurality of medical imaging devices based on medical imaging device status information that includes three dimensional position and attitude information of each of the plurality of medical imaging devices, wherein
the plurality of medical imaging devices includes a first medical imaging device of a first type and a second medical imaging device of a second type, different from the first type, and
the medical imaging device status information about the second medical imaging device includes information about a distance between the second medical imaging device and a focus point of the second medical imaging device;
select at least one medical image from among a plurality of medical images obtained by the plurality of medical imaging devices when the status of a corresponding medical imaging device satisfies a certain image decision condition, wherein the certain image decision condition includes that an observation target is included in the medical image;
determine whether or not the status of at least one of the plurality of medical imaging devices satisfies the certain image decision condition;
determine, when the first medical imaging device is tilted by a certain angle or more, that the status of the first medical imaging device satisfies the certain image decision condition;
determine, when the focus point of the second medical imaging device is aligned with the observation target, that the status of the second medical imaging device satisfies the certain image decision condition, and
select the at least one medical image from among a plurality of medical images obtained by the first medical imaging device and from among a plurality of medical images obtained by the second medical imaging device based on the respective status of the first medical imaging device and the second medical imaging device satisfying the certain image decision condition; and output the selected at least one medical image from the plurality of medical images obtained by the plurality of medical imaging devices.

2. The medical control device according to claim 1, wherein
the plurality of medical imaging devices includes at least one movable camera.

3. The medical control device according to claim 1, wherein
the first medical imaging device is a movable camera which is a point of view camera, and the second medical imaging device is a surgical field camera, which is installed in a stationary manner inside an operating room.

4. The medical control device according to claim 1, wherein
the processing circuitry is further configured to select at least two medical images from among the plurality of medical images obtained by the plurality of medical imaging devices.

5. The medical control device according to claim 1, wherein
the processing circuitry is further configured to discard any medical images of the plurality of medical images obtained by the plurality of medical imaging devices that are not selected.

6. The medical control device according to claim 1, wherein the processing circuitry is further configured to filter any remaining medical images of the plurality of medical images that are not selected by the processing circuitry by selectively displaying or recording only the selected at least one medical image.

7. The medical control device according to claim 1, wherein the medical imaging device status information further includes occlusion information and images of the plurality of medical images having the occlusion information indicating surgical field occlusion are not selected.

8. A medical control device for a medical imaging system, comprising:
processing circuitry configured to
determine a status of each of a plurality of medical imaging devices based on medical imaging device status information that includes three dimensional position and attitude information of each of the plurality of medical imaging devices, wherein
the plurality of medical imaging devices includes a plurality of movable cameras, and
the medical imaging device status information about each of the plurality of movable cameras includes information about a position of the respective movable camera and information about a distance between the respective movable camera and a respective focus point of the movable cameras;
select at least one medical image from among a plurality of medical images obtained by the plurality of medical imaging devices when a status of a corresponding medical imaging device satisfies a certain image decision condition, wherein the certain image decision condition includes that an observation target is included in the medical image;
determine whether or not the status of at least one of the plurality of medical imaging devices satisfies the certain image decision condition, wherein when the respective focus point of the respective movable camera is aligned with the observation target, the processing circuitry is configured to determine that the status of the respective movable camera satisfies the certain image decision condition; and
output the selected at least one medical image from the plurality of medical images obtained by the plurality of medical imaging devices.

9. The medical control device according to claim 8, wherein
at least one of the plurality of movable cameras is a wearable camera.

10. The medical control device according to claim 8, wherein
at least one of the plurality of movable cameras is attached to a treatment tool used in a medical procedure.

11. The medical control device according to claim 8, wherein
at least one of the plurality of movable cameras is a microscope camera that obtains an image of an observation target with a microscope being attached to a leading end of an arm.

12. The medical control device according to claim 8, wherein
at least one of the plurality of movable cameras is an endoscope camera that obtains an image of an observation target with an endoscope being attached to a leading end of an arm.

13. The medical control device according to claim 8, wherein
at least one of the plurality of movable cameras is an X-ray camera that obtains an X-ray tomographic image while moving relative to a patient body.

14. The medical control device according to claim 8, wherein
at least one of the plurality of movable cameras is configured to obtain an ultrasound image inside a blood vessel while moving a catheter provided with a transducer on a leading end, inside the blood vessel.

15. A medical control device for a medical imaging system, comprising:
processing circuitry configured to determine a status of each of a plurality of medical imaging devices based on medical imaging device status information that includes three dimensional position and attitude information of each of the plurality of medical imaging devices, wherein the plurality of medical imaging devices includes a first medical imaging device of a first type and a second medical imaging device of a second type, different from the first type, and the medical imaging device status information about the second medical imaging device includes information about a distance between the second medical imaging device and a focus point of the second medical imaging device,
select at least one medical image from among a plurality of medical images obtained by the plurality of medical imaging devices when the status of a corresponding medical imaging device satisfies a certain image decision condition, wherein the certain image decision condition includes that an observation target is included in the medical image;
determine whether or not the status of at least one of the plurality of medical imaging devices satisfies the certain image decision condition;
determine, when a focus point of the first medical imaging device is aligned with the observation target, that the status of the first medical imaging device satisfies the certain image decision condition;

determine, when the focus point of the second medical imaging device is aligned with the observation target, that the status of the second medical imaging device satisfies the certain image decision condition, and select the at least one medical image from among a plurality of medical images obtained by the first medical imaging device and from among a plurality of medical images obtained by the second medical imaging device based on the respective status of the first medical imaging device and the second medical imaging device satisfying the certain image decision condition; and output the selected at least one medical image from the plurality of medical images obtained by the plurality of medical imaging devices, wherein the second medical imaging device is a microscope camera configured to obtain an image of the observation target with a microscope attached to a leading end of an arm for the microscope camera, and the first medical imaging device is an endoscope camera configured to obtain an image of the observation target with an endoscope attached to a leading end of an arm for the endoscope.

16. A medical control device for a medical imaging system, comprising:

processing circuitry configured to determine a status of each of a plurality of medical imaging devices based on medical imaging device status information that includes three dimensional position and attitude information of each of the plurality of medical imaging devices, wherein the plurality of medical imaging devices includes an X-ray camera that obtains an X-ray tomographic image while moving relative to a patient body, and an ultrasound that obtains an ultrasound image inside a blood vessel while moving a catheter provided with a transducer for obtaining ultrasound images on a leading end inside the blood vessel, the medical imaging device status information about the X-ray camera includes information about a position of the X-ray camera, the medical imaging device status information about the ultrasound includes information about a position of the transducer;

select at least one medical image from among a plurality of medical images obtained by the plurality of medical imaging devices when a status of a corresponding medical imaging device satisfies a certain image decision condition, wherein the certain image decision condition includes that an observation target is included in the medical image;

determine whether or not the status of at least one of the plurality of medical imaging devices satisfies the certain image decision condition;

wherein the processing circuitry is further configured to determine, when the position of the X-ray camera corresponds to the position of the ultrasound, that the status of the X-ray camera satisfies the certain image decision condition, and select the at least one medical image from among an ultrasound image of the inside of the blood vessel obtained by the ultrasound and an X-ray tomographic image that includes a site being depicted by the ultrasound image from among a plurality of X-ray tomographic images depicting different sites in the patient body; and output the selected at least one medical image from the plurality of medical images obtained by the plurality of medical imaging devices.

17. The medical control device according to claim 16, wherein when the at least one medical image displayed on a display device includes the ultrasound image and the X-ray tomographic image, the processing circuitry is further configured to overlay onto the X-ray tomographic image an icon indicating the site being depicted by the ultrasound image.

18. A medical control method, comprising:

determining a status of each of a plurality of medical imaging devices based on medical imaging device status information that includes three dimensional position and attitude information of each of the plurality of medical imaging devices, wherein the plurality of medical imaging devices includes a plurality of movable cameras, and the medical imaging device status information about each of the plurality of movable cameras includes information about a position of the respective movable camera and information about a distance between the respective movable camera and a respective focus point of the movable camera;

selecting at least one medical image from among a plurality of medical images obtained by the plurality of medical imaging devices when the status of a corresponding medical imaging device satisfies a certain image decision condition, wherein the certain image decision condition includes that an observation target is included in the medical image;

determining whether or not the status of at least one of the plurality of medical imaging devices satisfies the certain image decision condition, wherein, when the respective focus point of the respective movable camera is aligned with the observation target, determining that the status of the respective movable camera satisfies the certain image decision condition; and outputting the selected at least one medical image from the plurality of medical images obtained by the plurality of medical imaging devices.

19. A medical imaging and control system, comprising:

a plurality of medical imaging devices; and processing circuitry configured to determine a status of each of a plurality of medical imaging devices based on medical imaging device status information that includes three dimensional position and attitude information of each of the plurality of medical imaging devices, wherein the plurality of medical imaging devices includes a plurality of movable cameras, and the medical imaging device status information about each of the plurality of movable cameras includes information about a position of the respective movable camera and information about a distance between the respective movable camera and a respective focus point of the movable camera;

select at least one medical image from among a plurality of medical images obtained by the plurality of medical imaging devices when the status of a corresponding medical imaging device satisfies a certain image decision condition, wherein the certain image decision condition includes that an observation target is included in the medical image;

determine whether or not the status of at least one of the plurality of medical imaging devices satisfies the certain image decision condition; and, when the respective focus position is aligned with the observation target, the processing circuitry is configured to determine that the status of the respective movable camera satisfies the certain image decision condition; and output the selected at least one medical image from the plurality of medical images obtained by the plurality of medical imaging devices.

\* \* \* \* \*